US007943631B2

(12) United States Patent
Tseng

(10) Patent No.: US 7,943,631 B2
(45) Date of Patent: May 17, 2011

(54) METHOD OF TREATING DRUG ADDICTION USING DEXTRO-MORPHINE

(75) Inventor: Leon F. Tseng, New Berlin, WI (US)

(73) Assignee: MCW Research Foundation, Inc., Milwaukee, WI (US)

( * ) Notice: Subject to any disclaimer, the term of this patent is extended or adjusted under 35 U.S.C. 154(b) by 118 days.

(21) Appl. No.: 12/034,438

(22) Filed: Feb. 20, 2008

(65) Prior Publication Data

US 2008/0200370 A1    Aug. 21, 2008

Related U.S. Application Data

(60) Provisional application No. 60/902,406, filed on Feb. 21, 2007.

(51) Int. Cl.
*A01N 43/42* (2006.01)
*A61K 31/44* (2006.01)
(52) U.S. Cl. ........................................ 514/282; 514/812
(58) Field of Classification Search .................. 514/282, 514/812
See application file for complete search history.

(56) References Cited

OTHER PUBLICATIONS

Horan B, Gardner EL, Dewey SL, Brodie JD, and Ashby CR, "The selective sigma(1) receptor agonist, 1-(3,4-dimethoxyphenethyl)-4-(phenylpropyl)piperazine (SA4503), blocks the acquisition of the conditioned place preference response to (−)-nicotine in rats," European Journal of Pharmacology, Aug. 2001, 426(1-2), R1-R2.*
Maurice T, Casalino M, Lacroix M, and Romieu P, "Involvement of the sigma 1 receptor in the motivational effects of ethanol in mice," Pharmacoloogy Biochemistry and Behavior, Mar. 2003, 74(4), 869-876.*
Romieu P, Phan VL, Martin-Fardon R, and Maurice T, "Involvement of the sigma(1) receptor in cocaine-induced conditioned place preference: possible dependence on dopamine uptake blockade," Neuropsychopharmacology, Apr. 2002, 26(4), 444-455.*
Stefanski R, Justinova Z, Hayashi T, Takebayashi M, Goldberg SR, and Su TP, "Sigma1 receptor upregulation after chronic methamphetamine self-administration in rats: a study with yoked controls," Psychopharmacology, Aug. 2004, 175(1), 68-75.*
Wu HE, Schwasinger ET, Terashvili M, and Tseng LF, "dextro-Morphine attenuates the morphine-produced conditioned place preference via the sigma(1) receptor activation in the rat," European Journal of Pharmacology, May 2007, 562(3), 221-226 (Epub Feb. 8, 2007).*
Monnet FP, Debonnel G, and de Montigny C, "In vivo electrophysiological evidence for a selective modulation of N-methyl-D-aspartate-induced neuronal activation in rat CA3 dorsal hippocampus by sigma ligands," Journal of Pharmacology and Experimental Therapeutics, Apr. 1992, 261(1), 123-130.*
Balfour et al.,"The Putative Role of Extra-Synaptic Mesolimbic dopamine in the Neurobiology of Nicotine Dependence," Behavioural Brain Research (2000) 113:73-83.

Bonci et al., "The Dopamine-containing Neuron: Maestro or Simple Musician in the Orchestra of Addiction?," TRENDS in Pharmacological Sciences (Apr. 2003) 24(4):172-177.
Contet et al., "Mu Opioid Receptor: A Gateway to Drug Addiction," Current Opinion in Neurobiology (2004) 14:370-378.
Dani et. al., "Synaptic Plasticity and Nicotine Addiction," Neuron (2001) 31:349-352.
De Vries, Taco J. and Shippenberg, Toni S., "Neural Systems Underlying Opiate Addiction," The Journal of Neurosciences (2002) 22(9):3321-3325.
Iijima et al., "Studies in the (+)-Morphinan Series. 4. A Markedly Improved Synthesis of (+)- Morphine," J. Org. Chem. (1978) 43(7):1462-1463.
Jacquet et al., "Stereospecific and Nonstereospecific Effects of (+)- and (−)- Morphine: Evidence for a New Class of Receptors," Science (1977) 198:842-845.
Joels, Marian, "Corticosteroid Effects in the Brain: U-shape it," TRENDS in Pharmacological Sciences (2006) 27 (5):244-250.
McCracken et al., "Two Novel Sigma Receptor Ligands, BD1047 and LR172, Attenuate Cocaine-Induced Toxicity and Locomotor Activity," European Journal of Pharmacology, (1999) 370:255-232.
Mei, J and Pasternak, G., "Sigma1 Receptor Modulation of Opioid Analgesia in the Mouse," The Journal of Pharmacology and Experimental Therapeutics (2002) 300(4):1070-1074.
Monnet, Francois and Tangui, Maurice, "The Sigma1 Protein as a Target fot the Non-genomic Effects of Neuro (active)steroids: Molecular, Physiological, and Behavioral Aspects," Journal of Pharmacological Sciences (2006) 100:93-118.
Mucha, Ronald and Herz, Albert, "Preference Conditioning Produced by Opioid Active and Inactive Isomers of Levorphanol and Morphine in Rat," Life Science (1986) 38:241-249.
Olmstead, Mary and Burns, Lindsay, "Ultra-low-dose Naltrexone Suppresses Rewarding Effects of Opiates and Aversive Effects of Opiate Withdrawal in Rats," Psychopharmacology (2005) 181:576-581.
Pilotte, Nancy S., "Neurochemistry of Cocaine Withdrawal," Current Opinion in Neurology (1997) 10:534-538.
Romieu et al., "Sigma1 Receptor-Related Neuroactive Steroids Modulate Cocaine-Induced Reward," The Journal of Neuroscience (2003) 23(9):3572-3576.
Shippenberg, Toni and Elmer, Gregory, "The Neurobiology of Opiate Reinforcement," Critical Reviews in Neurobiology, (1998) 12(4):267-303.
Terashvili et al., "Differential Conditioned Place Preference Responses to Endomorphin-1 and endomorpin-2 Microinjected into the Posterior Nucleus Accumbens Shell and Ventral Tegmental Area in the Rat," The Journal of Pharmacology and Experimental Therapeutics (2004) 309(2):816-824.

(Continued)

*Primary Examiner* — San-ming Hui
*Assistant Examiner* — Paul Zarek
(74) *Attorney, Agent, or Firm* — Quarles & Brady LLP; Sara D. Vinarov

(57) ABSTRACT

The present invention relates a method of treating drug addiction in an individual by administering to the addicted individual a therapeutically effective amount of dextro-morphine capable of activating an opioid receptor. It is disclosed here that dextro-morphine is suitable for treating addiction to natural opiates, semi-synthetic opiates, fully synthetic opioids, and endogenous opioid peptides, as well as nicotine.

21 Claims, 13 Drawing Sheets

OTHER PUBLICATIONS

Terashvili et al., "(+)-Morphine and (−)-Morphine Stereoselectively Attenuate the (−)-morphine-produced Tail-flick Inhibition via the Naloxone-sensitive Sigma Receptor in the Ventral Periaqueductal Gray of the Rat," European Journal of Pharmacology (2007) 571:1-7.

Terashvili et al., "(+)-Morphine attenuates the (−)-Morphine-produced Conditioned Place Preference and the Mu-opioid Receptor-mediated Dopamine Increase in the Posterior Nucleus Accumbens of the Rat," European Journal of Pharmacology (2008) 587:147-154.

Tsao, Li-i and Su, Tsung-Ping, "Naloxone-Sensitive, Haloperidol-Sensitive, [3H] (+)SKF-10047-Binding Protein Partially Purified From Rate Liver and Rat Brain Membranes: and Opioid/Sigma Receptor," Synapse (1997) 25:117-124.

Wu et al., "Opposite Conditioned Place Preference Response to Endomorphin-1 and Endomorphin-2 in the Mouse," Neuroscience Letters (2004) 365:157-161.

Wu et al., "Stereoselective Action of dextro-Morphine over levo-Morphine on Glia in the Mouse Spinal Cord," The Journal of Pharmacology and Experimental Therapeutics (2005) 314(3):1101-1108.

* cited by examiner

Injection sites at the posterior nucleus accumbens shell

METHOD OF TREATING DRUG ADDICTION USING DEXTRO-MORPHINE

CROSS-REFERENCE TO RELATED APPLICATIONS

This application claims the benefit of U.S. Provisional Application No. 60/902,406 filed Feb. 21, 2007. This application is incorporated herein by reference in its entirety.

STATEMENT REGARDING FEDERALLY SPONSORED RESEARCH OR DEVELOPMENT

This invention was made with United States government support awarded by the National Institutes of Health and the National Institute on Drug Abuse (NIH/NIDA) grant R01 DA12588-05. The United States has certain rights in this invention.

BACKGROUND OF THE INVENTION

Opioids are chemical substances that have a morphine-like action in the body. The main use is for pain relief. These agents work by binding to opioid receptors, which are found principally in the central nervous system and the gastrointestinal tract. Opioids include (1) natural opiates, such as (−)-morphine; (2) semi-synthetic opiates, such as heroin; (3) fully synthetic opioids, such as methadone; and (4) endogenous opioid peptides, produced naturally in the body, such as endorphins and enkephalins. The term opiate and opioid are used synonymously here. Although opiates technically cover natural opium alkaloids and the semi-synthetics derived from them.

Opioid addiction is recognized as a central nervous system disorder, caused by continuous opioid intake. The ability of opioids to cause addiction can be viewed as a form of neuronal plasticity (Dani et al., (2001) *Neuron* 31:349-352). Indeed, chronic opioid exposure has been shown to produce profound biochemical changes in specific brain regions thought to mediate the reinforcing or addicting actions of the drugs (Pilotte, (1997) *Curr. Opin. Neurol.* 10:534-538). The dopamine-containing neurons that originates in the ventral tegmental area (VTA) projecting primarily to the nucleus accumbens (Acb) and the prefrontal cortex are an integral part of the neural reward circuitry that has been shown to be crucial for self-stimulation, behavioral sensitization and the dependence produced by opioids (De Vies and Shippenberg, (2002) *J. Neurosci.* 22:3321-3325). Dopamine is the principal neurotransmitter and neuromodlator that mediates reinforcing effects.

It is well known that opioids cause functional changes in dopamine-containing neurons that spread widely within these neurons. This results in an increase of neuronal activity and dopamine release from these nerve terminals (Schultz, (2000) *Nat. Rev. Neurosci.* 1:199-207). Extended opioid use leads to the nerve cells in the brain to stop functioning as they normally would and stop producing natural endorphins. Because the body is getting opioids and no longer is producing endorphins the nerve cells start to degenerate and cause a physical dependency on opioids. Sudden withdrawal (quitting cold turkey) leads to a syndrome called withdrawal syndrome. Withdrawal syndrome is a long and painful process and can result in permanent damage to the cardiopulmonary system and the central nervous system. Untreated and unmonitored, it can result in death for unhealthy individuals. For these reasons, opioids dependency treatment requires appropriate and responsible medical care.

Traditionally there have been several forms of opioid detoxification including opioid agonist drugs. These include drugs like methadone, levo-alpha-acetylmethadol (LAAM), or Buprenorphine; Clonidine, which blocks some withdrawal symptoms; ultra-rapid opioid detox under anesthesia; and an experimental method using the drug lofexidine. Opioid agonist drugs act like opioids but do not produce the same high and are administered in doses that are gradually reduced. Since these medications act like opioids there appear to be no noticeable or significantly reduced withdrawal symptoms.

Clonidine can be administered by a transdermal patch, which dispenses the drug gradually and consistently over a seven-day period. Individuals who choose to use the patch should also take Clonidine orally for the first two days since medications taken through the skin takes two days to reach a steady effectiveness. Monitoring of blood pressure is essential since Clonidine causes hypotension and sedation.

Another method of treating Rapid detox is done under general anesthesia with intubations for six to eight hours. During this time a combination of drugs, usually naltrexone and Clonidine are administered to the individual. Lofexidine, a non-addictive drug brought to the market in 1992, is a centrally acting alpha-2 adrenergic agonist targeted for relief of opioid withdrawal symptoms.

Withdrawal symptoms continue to be the greatest obstacle in heroin detoxification treatment. Studies show that there is no proof that one detoxification treatment is better than another. Relapses continue to occur in numerous cases around the world therefore making opioid addiction very difficult to treat successfully long term. Studies show that on average addicts will stop and start detox 10-25 times in their lifetime relapsing back to opioid use each and every time.

Statistics and studies show that there is no easy cure for opioid treatment and there is no guarantee that a relapse will not happen. New methods to use for opioid detox, one must choose the method that looks at their general health condition, psychological state, external support and length of time addicted and making an informed decision that best meets the needs of the individual. Therefore, alternative methods effective for treatment of addition would be a desirable contribution to the art.

BRIEF SUMMARY OF THE INVENTION

The present invention is broadly summarized as a novel method for clinically treating drug addiction in an individual by administering to the addicted individual a therapeutically effective amount of pharmacologically active compound having (+)-morphine, wherein the (+)-morphine is effective by activating a sigma receptors to attenuate the (−)-opiate-produced addiction. Specifically, in one aspect, the invention presented here is a method of treating opioid addiction in a mammal by administering an effective amount of (+)-morphine to the mammal, wherein (+)-morphine activates the naloxone-sensitive sigma receptor. The term dextro-morphine and (+)-morphine are used synonymously here.

In another aspect of the invention, the (+)-morphine is administered orally, intravenously, intraperitoneally, subcutaneously, or transdermally.

In another aspect of the invention, the (+)-morphine may be administered to the individual prior to (e.g., pretreatment), simultaneously with or subsequent to intaking the addictive drug.

In another aspect of the invention, a human is pretreated with an effective dose of (+)-morphine, wherein the pretreatment dosage is from about 1 µg/kg to about 5 µg/kg given subcutaneously; from about 0.2 µg/kg to about 1 µg/kg given intraveneously; from about 5 µg/kg to about 25 µg/kg given orally; from about 1.0 µg/kg to about 5 µg/kg given intraperitoneally.

In another aspect of the invention, an effective dose of (+)-morphine is administered by pulse-dosing, wherein the pulse-dose is repeated as needed by the individual.

In another aspect of the invention, a effective dose of (+)-morphine is administered as a single or multiple dose daily of about 0.5 mg to about 5 mg in a human.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

DETAILED DESCRIPTION OF THE INVENTION

Figure 1:
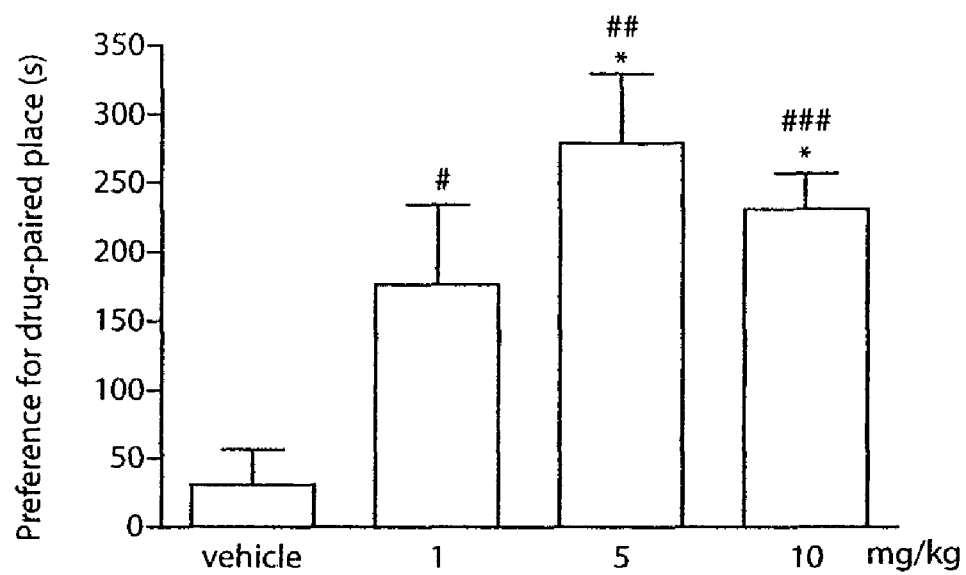
FIG. 1 shows that (−)-morphine sulfate given subcutaneously dose-dependently produced the place conditioning in rats. Groups of rats were injected subcutanesously with a various dose of (−)-morphine sulfate (1-10 mg/kg) alternatively with saline vehicle and place in the conditioning box right after the injection for 40 min twice a day from $2^{nd}$ day for 3 days for place conditioning. The free movement for each rat was measured for 15 min in pre- and post-conditioning on the 1st and 5th day, respectively. Each column represents the mean and the vertical bar represents the S.E.M. with 8 rats in each group. The one-way ANOVA followed by Dunnett's post-test was used to test the difference between groups; the F $(3,28)=6.097$; *p<0.01 compared with the vehicle injected group. Paired Student t-test was used to test whether individual dose produced conditioned place preference or conditioned place aversion; #p<0.05, ##p<0.01, ###p<0.001.

The present invention broadly relates to a novel method for clinically treating drug addiction in an individual by administering to the addicted individual a therapeutically effective amount of pharmacologically active compound having (+)-morphine (dextro-morphine). The anti-addictive effect of dextro-morphine was discovered through place conditioning experiments, where it was found that conditioned place preference (CPP) was produced by (−)-morphine. From these CPP experiments, it was found that (+)-morphine given systemically blocks the systemic (−)-morphine-produced CPP through activation of the naloxone-sensitive sigma receptor originally proposed by Tsao and Su (1997) (*Synapse*, 25:117-124, 1997).

It is described here for the first time that attenuation of the (−)-morphine-produced tail-flick inhibition induced by dextro-morphine is reversed by the sigma receptor antagonist BD1047 and by (+)-naloxone, indicating that attenuation of the (−)-morphine analgesia is mediated by the naloxone-sensitive sigma receptor activation. Sigma receptors have been reported to play an important role in the modulation of analgesia produced by μ-, δ- or κ-opioid receptor agonists (Mei, J., Pasternak, G. W., (2002) *J. Pharmacol. Exp. Ther.* 300,1070-1074) and the CPP produced by nicotine, cocaine, amphetamine or alcohol (Liu, Y.et al. (2005) *J. Pharmacol. Exp. Ther.* 314, 770-779). The experiment was then undertaken to determine if the blockade of sigma receptors by BD1047 reverses the attenuation of the (−)-morphine-produced CPP induced by dextro-morphine. Applicant discloses for the first time that BD1047 pretreatment reverses the attenuation of the morphine-produced CPP induced by dextro-morphine pretreatment. The finding provides the evidence that activation of sigma receptors is involved in the anti-CPP induced by dextro-morphine. As such, dextro-morphine can be developed as an antidote for the clinical treatment of opiate addiction.

Accordingly, in one embodiment, the invention provides a method of treating opioid addiction in a mammal by administering an effective amount of dextro-morphine to the mammal, wherein dextro-morphine activates the naloxone-sensitive sigma receptor.

In another embodiment of the invention, the dextro-morphine is administered orally, intravenously, intraperitoneally, subcutaneously, intrathecally, or transdermally.

In another embodiment of the invention, the dextro-morphine may be administered to the individual prior to (e.g., pretreatment), simultaneously with or subsequent to intaking the addictive drug.

In another embodiment of the invention, a human is pretreated with an effective dose of (+)-morphine, wherein the pretreatment dosage is from about 1 μg/kg to about 5 μg/kg given subcutaneously; from about 0.2 μg/kg to about 1 μg/kg given intraveneously; from about 5 μg/kg to about 25 μg/kg given orally; from about 1.0 μg/kg to about 5 μg/kg given intraperitoneally.

In another embodiment of the invention, an effective dose of (+)-morphine is administered by pulse-dosing, wherein the pulse-dose is repeated as needed by the individual.

In another embodiment of the invention, a effective dose of (+)-morphine is administered as a single or multiple dose daily of about 0.5 mg to about 5 mg in a human.

For convenience, certain terms employed in the specification, examples, and appended claims are described here.

As used herein the term "individual" refers to any animal classified as a mammal, including humans, domestic and farm animals, and zoo, sports, or pet animals, such as dogs, cats, cattle, rats, horses, sheep, pigs, goats, rabbits, etc. Preferably, the mammal is human.

As used herein, the term "addiction" broadly encompasses the process whereby physical and/or psychological dependence develops to a drug—including opioids. The withdrawal symptoms can reinforce the addiction, driving the user to continue taking the drug. Drug addiction is considered a pathological state. The disorder of addiction involves the progression of acute drug use to the development of drug-seeking behavior, the vulnerability to relapse, and the decreased, slowed ability to respond to naturally rewarding stimuli. The Diagnostic and Statistical Manual of Mental Disorders, Fourth Edition (DSM-IV) has categorized three stages of addiction: preoccupation/anticipation, binge/intoxication, and withdrawal/negative affect. These stages are characterized, respectively, by constant cravings and preoccupation with obtaining the substance; using more of the substance than necessary to experience the intoxicating effects; and experiencing tolerance, withdrawal symptoms, and decreased motivation for normal life activities.

The term "drug addiction" as used herein is a state of periodic or chronic intoxication produced by the repeated consumption of a drug (natural or synthetic). Its characteristics include: (i) an overpowering desire or need (compulsion) to continue taking the drug and to obtain it by any means; (ii) a tendency to increase the dose; (iii) a psychic (psychological) and generally a physical dependence on the effects of the drug; and (iv) detrimental effects on the individual and on society.

As used herein, the term "opioid" broadly encompasses a chemical substance that has a morphine-like action in the body. The main use is for pain relief. These agents work by binding to opioid receptors, which are found principally in the central nervous system and the gastrointestinal tract. The receptors in these two organ systems mediate both the beneficial effects, and the undesirable side effects. There are a number of broad classes of narcotics:

(1) natural opiates—opium alkaloids contained in the resin of the opium poppy including but not limited to morphine, opium, codeine, thebaine, papaverine, and noscapine;

(2) semi-synthetic opiates—created from the natural opioids, including but not limited to hydromorphone, hydrocodone, oxycodone, and heroin;

(3) fully synthetic opioids—including but not limited to fentanyl, pethidine, methadone, and propoxyphene;

(4) endogenous opioid peptides—produced naturally in the body, including but not limited to endorphins, enkephalins, dynorphins, and endomorphins.

The archetypal opioid, naturally occurring morphine alkaloid, which is isolated from the juice of the opium poppy, papaver somniferum, is stereochemically identified as a levorotatory form, (−)-morphine. (−)-Morphine and various other substances (e.g., codeine, oxycodone, hydrocodone, diamorphine, pethidine) all exert a similar influence on the cerebral opioid receptor system. (−)-Morphine interacts with μ-opioid receptors to produce potent analgesic, addictive and other pharmacological effects. The dextrorotatory dextro-morphine, which is synthesized from sinomenine (Iijima et al., (1978) *J. Org. Chem.* 43;1462-1463), does not have any affinity for μ-opioid receptors and therefore does not produce any μ-opioid receptor mediated pharmacological effects (Jacquet et al., (1977) *Science* 198:842-845). However, it was previously demonstrated that dextro-morphine pretreatment attenuates the analgesia produced by (−)-morphine in mice (Wu et al., 2005).

The present invention encompasses not only the opioids identified above, but also natural and synthetic opioid-like compounds including but not limited to nicotine and cocaine (a dopamine reuptake inhibitor). Because of the way these compounds affect the mesolimbic reward pathway, they are addictive. Notably, the pharmacological and behavioral characteristics that determine tobacco addiction are similar to those that determine addiction to drugs such as heroin and cocaine.

Opioids, while very effective analgesics, may have some unpleasant side-effects. Up to 1 in 3 individuals starting morphine may experience nausea and vomiting (generally relieved by a short course of antiemetics). Pruritus (itching) may require switching to a different opioid. Constipation occurs in almost all individuals on opioids, and laxatives (lactulose, macrogol-containing or co-danthramer) are typically co-prescribed.

When used appropriately, opioids and similar narcotic analgesics are otherwise safe and effective; however risks such as addiction and the body becoming used to the drug can occur. Due to the body getting used to the drug often the dose must be increased if it is for a chronic disease this is where the no ceiling limit of the drug comes into play. However what must be remembered is although there is no upper limit there is a still a toxic dose even if the body has become used to lower doses. Dosing of all opioids may be limited by opioid toxicity (confusion, respiratory depression, myoclonic jerks and pinpoint pupils), but there is no dose ceiling in individuals who tolerate this.

Opioids bind to specific "opioid receptors" in the central nervous system and in other tissues. There are three principal classes of opioid receptors, μ, κ, δ (mu, kappa, and delta), although up to seventeen have been reported, and include the ε, ι, λ, and ζ (Epsilon, Iota, Lambda and Zeta) receptors. μ-Opioid receptors in the mesolimbic dopaminergic system have been proposed to be the gateway to drug addition (Contet et al., (2004) *Curr. Opin. Neurobiol.* 14:370-378).

Alternatively, σ (Sigma) receptors described herein are not considered opioid receptors because they: (1) are not reversed by the opioid antagonist naloxone; (2) do not exhibit high-affinity binding for ketamine and phencyclidine; and (3) are stereoselective for dextro-rotatory isomers while the other opioid receptors are stereo-selective for levo-rotatory isomers. As used herein, the term "sigma receptor" refers to the human sigma 1 opioid receptor (OPRS1), which has a cDNA sequence defined by GenBank Accession No. BC004899, incorporated by reference in its entirety herein. This gene is known to encode a receptor protein that interacts with a variety of psychotomimetic drugs, including cocaine and amphetamines. Sigma receptors are non-opioid and non-phencyclidine receptors that contain two subtypes: sigma-1 and sigma-2 receptors. The sigma-1 receptor has been cloned its sequence does not resemble any mammalian receptor protein. It contains 223 amino acid and resides primarily at the endoplasmic reticulum, existing mainly in the CNS and its periphery.

As used herein, "conditioned place preference" (CPP) refers to one of the most popular models to study the motivational effects of drugs and non-drug treatments in experimental animals. Studies in humans as well as experimental animals have shown that the rewarding effects of drugs can be classically conditioned to stimuli previously associated with their administration. (O'brien C. P. et al. (1986) Classical conditioning in human opioid dependence, *Behavioral Analysis of Drug Dependence*, Goldberg, S. R. a. S., I.P., Ed, Academic Press, New York, 1986, 329-356). Since 1998, more than 1000 new studies using place conditioning have been published. Place conditioning is increasingly used to assess the motivational effects of drugs or non-drug rewards. Place conditioning continues to be widely used to study tolerance and sensitization to the rewarding effects of drugs induced by pre-treatment regimens.

The CPP experimental model is generally acceptable as an experimental model for humans. The CPP model for evaluating addiction in rats and mice is well established and accepted by researchers as a suitable model for predicting human addiction and treatment thereof. Most of the addictive drugs used by human produce CPP in rats. Review articles that support the use of animal CPP to evaluate human addiction results include, for example, Toni S. Shippenberg and Gregory I. Elmer (1998) The neurobiology of opiate reinforcement, *Critical Reviews in Neurobiology*, 12(4): 267-303; Tzchentke T M (2007) Measuring reward with conditioned place preference PP) paradigm; update of the last decade, *Addict Biol* 12(3-4):227-462; and Sanchis-Segura C and Spanagel R, (2006) Behavioral assessment of drug reinforcement and addictive features in rodents: an overview, *Addict Biol* 11(1) 2-38.

The role of sigma-1 receptors in the CPP produced by cocaine, amphetamine, alcohol and nicotine has been studied in the literature. These reports suggest that sigma-1 receptor activation modulates differently for the CPP induced by nicotine and by cocaine, amphetamine or alcohol via different neural pathways. As disclosed herein, blockade of the sigma receptors by BD1047 reversed the attenuation of the (−)-morphine-induced CPP by dextro-morphine, indicating that dextro-morphine attenuates the morphine CPP via sigma receptor activation.

As used herein, the term "opioid antagonists" includes but is not limited to Nalmefene, Naloxone, and Naltrexone.

In accordance with the invention, opioids may be taken either orally (in pill or liquid form), by injection into a muscle or vein as necessary (or as part of an intravenous [IV]. line), as an anal suppository, or as a patch attached to the skin. The dosage prescribed may vary widely depending on the individuals (e.g., weight), the addiction being treated, and whether or not other medications are also being taken.

As used herein, "the reward circuit" refers to the mesolimbic system, which is characterized by the interaction of several areas of the brain. When examining the biological basis of drug addition, one must first understand the pathways in which drugs act and how drugs can alter those pathways. The VTA consists of dopaminergic neurons which respond to glutamate. These cells respond when stimuli indicative of a reward are present. The VTA supports learning and sensitization development and releases dopamine (DA) into the forebrain. These neurons also project and release DA into the nucleus accubems, through the mesolimbic pathway. Virtually all drugs causing drug addiction increase the dopamine release in the mesolimbic pathway, in addition to their specific effects.

The nucleus accumbens (Acb) consists mainly of medium-spiny projection neurons (MSNs), which are glutamatergic neurons. The Acb is associated with acquiring and eliciting conditioned behaviors and involved in the increased sensitivity to drugs as addiction progresses.

The prefrontal cortex, more specifically the anterior cingulate and orbitofrontal cortices, is important for the integration of information which contributes to whether a behavior will be elicited. It appears to be the area in which motivation originates and the salience of stimuli is determined. The basolateral amygdala projects into the Acb and is thought to be important for motivation as well. More evidence is pointing towards the role of the hippocampus in drug addiction because of its importance in learning and memory. Much of this evidence stems from investigations manipulating cells in the hippocampus alters dopamine levels in Acb and firing rates of VTA dopaminergic cells.

It is generally accepted that abused drugs such as opiates, nicotine, cocaine, amphetamine and alcohol share the common neural substrates mainly mesolimbic dopaminergic system for inducing drug addiction. The dopamine-containing neurons that originate in the VTA projecting primarily to the Acb and the prefrontal cortex are an integral part of the neural reward circuitry that has been shown to be crucial for self-stimulation, behavioral sensitization and the dependence produced by several drugs of abuse. All these drugs cause the increased release of dopamine and increase the dopamine receptor activity. The mesolimbic dopaminergic region, such as Acb and amygdale, appears to contain high density of sigma-1 receptor binding. Thus, the brain sites sensitive to dextro-morphine for attenuating the CPP and the dopamine release induced by morphine and nicotine are disclosed herein.

As used herein, the term "sigma receptor antagonist" may refer to DB1047 (N-[2-(3,4-Dichlorophenyl)ethyl]-N-methyl-2-(dimethylamino)ethylamine dihydrobromide). The attenuation of the (−)morphine-produced CPP was reversed by the pretreatment with the sigma receptor antagonist DB1047.

An "effective amount" or a "therapeutically effective amount" of dextro-morphine as disclosed herein is an amount sufficient to inhibit lymphoma cell growth. An "effective amount" may be determined empirically and in a routine manner, in relation to the stated purpose. More specifically, the term "therapeutically effective amount" refers to an amount of dextro-morphine effective to "treat" a disease or disorder in a subject or mammal.

As used herein the terms "treat", "treating" or "treatment" refer to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

A subject or mammal is successfully "treated" for addiction if, after receiving a therapeutic amount of dextro-morphine according to the methods of the invention, the individual shows observable and/or measurable reduction in or absence of one or more of the following side effects of drug addiction, such as but not limited to, for example, a decrease in the desire to continue to take the drug and a decrease in the psychological and physical withdrawal symptoms described herein.

The above parameters for assessing successful treatment and improvement in the addiction are readily measurable by routine procedures familiar to a physician.

In another embodiment, it is contemplated that dextro-morphine is administered in a pharmaceutical composition containing a pharmaceutically acceptable carrier. Such as carrier includes pharmaceutically acceptable carriers, excipients, or stabilizers which are nontoxic to the cell or mammal being exposed thereto at the dosages and concentrations employed. A carrier may be liquid or solid and suitable for oral administration. Examples of physiologically acceptable carriers include buffers; antioxidants; low molecular weight polypeptide; proteins; hydrophilic polymers; amino acids; carbohydrates; chelating agents; sugar alcohols; salt-forming counterions; and/or nonionic surfactants.

A pharmaceutically acceptable salt of dextro-morphine includes, but is not limited to, acid addition salts formed by mixing a solution of dextro-morphine with a solution of a pharmaceutically acceptable acid. The pharmaceutically acceptable acid may be hydrochloric acid, methanesulphonic acid, fumaric acid, maleic acid, succinic acid, acetic acid, benzoic acid, oxalic acid, citric acid, tartaric acid, carbonic acid or phosphoric acid. Various pharmaceutically acceptable salts are well known in the art and may be used with instant compound such as those disclosed in (Berge S M et al., "Pharmaceutical Salts." *J. Pharm. Sci.* 66:1-19 (1977) and Haynes D A et al., "Occurrence of pharmaceutically acceptable anions and cations in the Cambridge Structural Database," *J. Pharm. Sci.* 94:2111-2120 (2005), which are hereby incorporated herein by reference. For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

In a preferred embodiment, the pharmaceutical composition maybe in the form of a tablet or capsule. The dextro-morphine pharmaceutical composition may include an additional active agent. It is also envisioned that the dextro-morphine pharmaceutical composition maybe co-administered with other compounds for the treatment opioid addiction.

As used herein, the term "administration" means alone or "in combination with" one or more further therapeutic agents includes simultaneous (concurrent) and consecutive administration in any order. In addition to oral administration, it is contemplated that the dextro-morphine compound may be administered to humans for therapy by other suitable routes of administration, including nasally, as by, for example, a spray, rectally, intravaginally, parenterally (intravenous (IV), subcutaneous, or intramuscular injection), intrathecally, intracistemally and topically, as by powders, ointments or drops, including buccally and sublingually.

Regardless of the route of administration selected, the dextro-morphine compositions of the present invention may be used in a suitable hydrated form, and/or pharmaceutical composition formulated into pharmaceutically-acceptable dosage forms, such as described below or by other conventional methods known to those of skill in the art, without being toxic to the individual.

Accordingly, it is envisioned that the dosage levels will vary depending upon a variety of factors. Such factors include the activity of the dextro-morphine compound employed, or the ester, salt or amide thereof, the route of administration, the time of administration, the rate of excretion of the particular compound being employed, the duration of the treatment, other drugs, compounds and/or materials used in combination with the particular apoptosis-inducing agent employed, the age, sex, weight, condition, general health and prior medical history of the individual being treated, and like factors well known in the medical arts. A physician or veterinarian having ordinary skill in the art can readily determine and prescribe the effective amount of the pharmaceutical composition required.

In general, a suitable daily dose of a dextro-morphine compound of the invention will be that amount of the compound, which is the lowest dose effective to produce a therapeutic effect. Such an effective dose will depend upon the factors described above.

It is contemplated that a preferred dosage (preferably oral) ranges from about 1 mg to 5 mg/day of dextro-morphine for treatment of addiction. More preferably, it is envisioned that an effective treatment of addiction would require an oral formulation of the dextro-morphine compound given 2 to 3 times/day ranging from about 1 mg to 5 mg/day for at least 2 weeks per treatment. More preferably, the dosage would range from about 1 to 5 mg/day for at least 2 weeks per treatment alone or in combination with other therapeutic agents.

It is to be understood that this invention is not limited to the particular methodology, protocols, animal species, and reagents described, as such may vary. It is also to be understood that the terminology used herein is for the purpose of describing particular embodiments only, and is not intended to limit the scope of the present invention which will be limited only by the appended claims.

Materials and Methods

Animals

Male CD rats weighing 300-350 g (Charles River Breeding Laboratory, Wilmington, Mass.) were used. Animals were housed two per cage in a room maintained at 22±0.5° C. with an alternating 12-h light-dark cycle. Food and water were available ad libitum. Each animal was used only once. All experiments were approved by and conformed to the guidelines of the Animal Care Committee of the Medical College of Wisconsin.

Conditioned Place Preference (CPP)

An unbiased conditioned place preference paradigm was used to evaluate the effect of (+)-morphine pretreatment on the conditioned place preference produced by (−)-morphine. The place conditioning experiment consists of pre-conditioning, conditioning and post-conditioning phases (Terashvili et al., (2004) *J. Pharmacol. Exp. Ther.* 309, 816-824). Injections of vehicle or drug were only done during the conditioning phase. A two-compartment box (60×29.2×29.2 cm) with a transparent Plexiglas front separated by a gray cylinder platform (10.3 cm in diameter and 12 cm in height) was used. One compartment was white with a textured floor and the other was black with a smooth floor. For pre-conditioning, rats were initially placed on the neutral cylinder gray platform and allowed to step down off of the platform to either the white or black compartment. A sliding wall was then put down on the platform and the rat was free to access either compartment through two openings (9.5×12 cm) on each side of the platform. The amount of time spent in the black or white compartment was manually measured for 15 min. For pre-conditioning control, rat was tested once in the morning for their preference one day before conditioning sessions; only those rats that did not exhibit a significant preference between black and white compartments (350-550/900 s) were used for experiments. Rats, which spent less than 5 min 50 s in either the white or black compartment, were considered not to be neutral in preference for either side and were excluded from further study (less than 5% of rats).

The place conditioning session was carried out on days 2 to 4. The box was divided into two equal-sized compartments by putting down a sliding wall after removal of the gray cylinder platform. Conditioning session was conducted twice daily, morning and afternoon, and repeated for 3 days. Rats were placed in either the black or white compartment immediately following the injection and left in that compartment for 40 min. Forty min is in agreement with previous studies (Shippenberg and Heidbreder, (1995) *Eur. J. Pharmacol.* 280, 55-61). Rats were confined to either the black or white compartment after injection of drugs tested in the morning session of each day, and were confined to the opposite compartment after the injection of vehicle for the afternoon session and vice versa. Animals receiving vehicle in both sessions served as controls. Drug treatment consisted of dextro-morphine or BD1047 (N-[2-(3,4-Dichlorophenyl)ethyl]-N-methyl-2-(dimethylamino)ethylamine dihydrobromide) given intraperitoneally or morphine sulfate given subcutaneously. The morning session will be carried out from 8-11 a.m. and the afternoon session will be carried out from 2-5 p.m. of the day.

The post-conditioning session was carried out on day 5 and is exactly the same as the pre-conditioning. The scores for the drug-paired place are then calculated by subtracting the pre-conditioning score from post-conditioning score. A positive score represents conditioning place preference (CPP), while a negative score represents conditioning place aversion.

Drugs and Drug-Administration (−)-Morphine sulfate and (+)-morphine base were obtained from the National Institute on Drug Abuse (Baltimore, Md.). N-[2-(3,4-Dichlorophenyl)ethyl]-N-methyl-2-(dimethylamino)ethylamine dihydrobromide (BD1047) was purchased from Tocris (Ellisville, Mo.). (−)-Morphine and BD1047 were dissolved in 0.9% saline. The (+)-morphine was dissolved in 10 N hydrochloric acid and then titrated with 1 N sodium hydroxide to pH 7, which was then diluted to the intended dose in 0.9% saline. Drugs were injected subcutaneously or intraperitoneally in an injection volume of 0.1 ml per 100 g body weight with a 26-gauge needle.

Side Effects and Toxicity of (+)-morphine

The naturally occurring morphine, which is isolated from the juice of the opium poppy, papaver somniferum, is stereochemically identified as the (−)-isoform. (−)-Morphine produces analgesia, which is used clinically for the treatment of pain. However, (−)-morphine also produces a wide spectrum of unwanted effects, including respiratory depression, dysphoria, euphoria and constipation. The analgesia and untoward effects produced by (−)-morphine are mediated by the stimulation of μ-opioid receptors. The synthetic (+)-isomer of morphine, (+)-morphine, which is synthesized from alkaloid sinomenine does not have any appreciable affinity for μ-opioid receptors and therefore does not produce analgesic and other side effects produced by (−)-morphine (Jacquet Y F, et al. (1977) *Science* 198: 842-845). Mucha R F and Herz A (1986) *Life Sci* 38:241-249, reports that (+)-morphine (4 mg/kg, s.c.) given systemically does not produce any conditioned place preference nor does it produce any conditioned place aversion. (−)-Morphine at the same dose, on the other hand, produces marked conditioned place preference. The toxicity of (+)-morphine would be expected very low.

Statistical Analysis

Conditioning scores were expressed as mean ±S.E.M. The Student paired t-test was used to analyze the differences of the score between pre- and post-conditioning of each group of rats. One-way analysis of variance (ANOVA) followed by Dunnett's post-test was used to compare the difference between drug treated groups and the vehicle treated group. In all experiments, $p<0.05$ was considered a significant difference. The Prism statistical software was used to perform the statistics (version 4.1; GraphPad Software, Inc., San Diego, Calif.).

EXAMPLES

Example 1

Effect of (−)-morphine Sulfate Given Subcutaneously on the Production of the Conditioned Place Preference (CPP)

Groups of rats were injected subcutaneously with different doses of (−)-morphine sulfate (1, 5 or 10 mg/kg) or saline vehicle and placed in the CPP box immediately for place conditioning. (−)-Morphine sulfate at a dose, 1 and 5 mg/kg, dose-dependently produced CPP. However, (−)-morphine sulfate at a higher dose, 10 mg/kg, produced no more increase of the CPP. Subcutaneous injection of the vehicle did not affect the baseline place conditioning response (FIG. 1). Five mg/kg of (−)-morphine sulfate was then chosen for the experiments described in Examples 2 and 3 below.

Example 2

Figure 2:
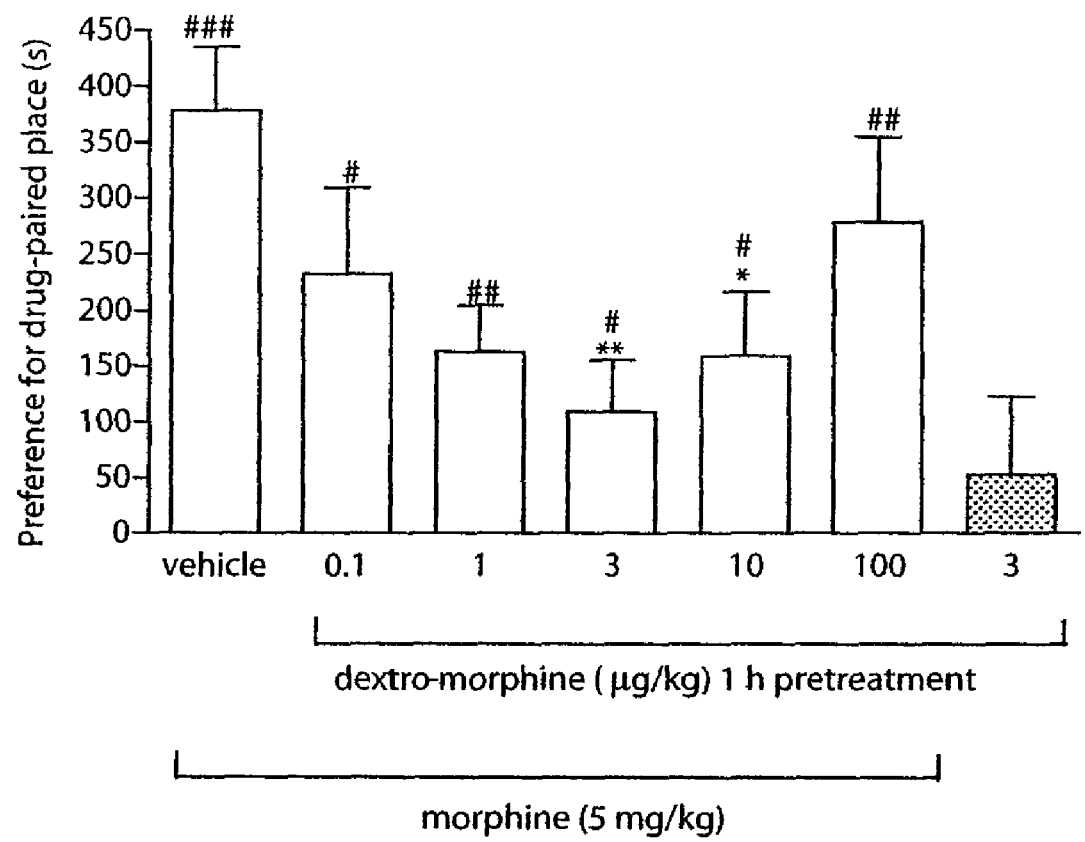
FIG. 2 shows that the increased conditioned place preference (CPP) produced by (−)-morphine sulfate is attenuated dose-dependently by (+)-morphine pretreatment in rats. Groups of rats were pretreated intraperitoneally with a various doses of (+)-morphine in the home cage for 1 h before subcutaneous injection of morphine sulfate (5 mg/kg) and were placed in the conditing box for place conditioning. The free movement for each rat was measured for 15 min in pre- and post-conditioning on the 1st and 5th day, respectively. Each column represents the mean and the vertical bar represents the S.E.M. with 8-12 rats in each group. The one-way ANOVA followed by Dunnett's post-test was used to test the difference between groups; the F $(5,51)=2.695$; *p<0.05, **p<0.01 compared with the vehicle injected group. Paired Student t-test was used to test whether individual dose produced conditioned place preference or conditioned place aversion; #p<0.05, ##p<0.01, ###p<0.001. The dextro-morphine (3 µg/kg) given intraperitoneally alone served as control group, which did not include in the statistical test (the first column from the right) and produced neither conditioning place preference or conditioned place aversion.

Effects of (+)-morphine Given Intraperitoneally on the CPP Produced by (−)-morphine Sulfate Given Subcutaneously Groups of rats were pretreated intraperitoneally in the home cage with different doses (0.1-100 μg/kg) of (+)-morphine or saline vehicle for 1 h before subcutaneously injection of (−)-morphine sulfate (5 mg/kg) and were placed in the CPP box for place conditioning. Pretreatment with (+)-morphine at a dose from 0.1 to 3 μg/kg dose-dependently attenuated the (−)-morphine-produced CPP. However, (+)-morphine at a higher dose 100 μg/kg did not attenuate the (−)-morphine-produced CPP (FIG. 2). Thus, (+)-morphine at a dose range from 0.1 to 100 μg/kg produced a U-shaped dose-response curve with a maximal inhibition at 3 μg/kg for attenuating the morphine-produced CPP. Pretreatment with (+)-morphine (3 μg/kg) given intraperitoneally alone did not affect the baseline place conditioning in rats treated subcutaneously with saline vehicle (FIG. 2).

Example 3

Figure 3:
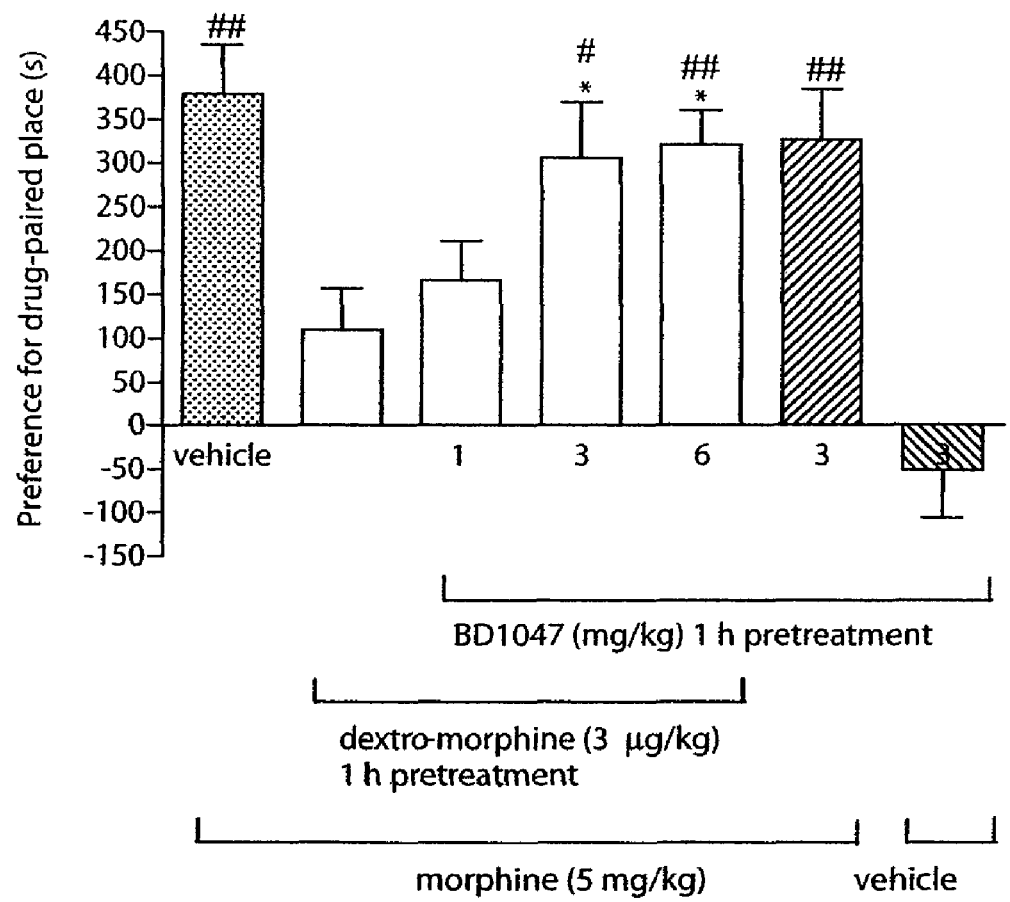
FIG. 3 shows that the attenuation of the (−)-morphine-produced conditioned place preference induced by (+)-morphine is reversed by the sigma receptor antagonist BD1047 pretreatment. Groups of rats were pretreated intraperitoneally with a various dose of BD1047 (1, 3 or 6 mg/kg) and 3 µg/kg of (+)-morphine in the home cage for 1 h before subcutaneous injection of (−)-morphine sulfate (5 mg/kg) or vehicle and were placed in the conditioning box for place conditioning. The free movement for each rat was measured for 15 min in pre- and post-conditioning on the 1st and 5th day, respectively. Each column represents the mean and the vertical bar represents the S.E.M. with 8-11 rats in each group. The first column from the left and the first two columns from the right represented the control-group data, which did not include in the statistical analysis. The one-way ANOVA followed by Dunnett's post-test was used to test the difference between groups; the F $(5,51)=2.695$; *p<0.05, **p<0.01 compared with the vehicle injected group. Paired Student t-test was used to test whether individual dose produced conditioned place preference or conditioned place aversion; #p<0.05, ##p<0.01, ###p<0.001.

Effects of Sigma Receptor Antagonist BD1047 Given Intraperitoneally on the Attenuation of (−)-morphine-produced CPP Induced by (+)-morphine Since most (+)-opiates such as (+)-pentazocine and (+)-N-allyl-normetazocine interact stereospecifically with the sigma-1 receptors, the possibility that the sigma-1 receptors are involved in the (+)-morphine-induced anti-CPP was then explored. The sigma-1 receptor antagonist BD1047 was used to determine if the blockade of the sigma-1 receptors by BD1047 pretreatment would reverse the attenuation of the morphine-produced CPP induced by (+)-morphine. Groups of rats were pretreated intraperitoneally in the home cage with a dose 1, 3 or 6 mg/kg of BD1047 and 3 μg/kg of (+)-morphine for 1 h before subcutaneously injection of morphine sulfate (5 mg/kg) and were place in the CPP box for place conditioning. Pretreatment with BD1047 dose-dependently reversed the attenuation of the morphine-produced CPP produced by morphine (FIG. 3). Pretreatment with BD1047 (3 mg/kg) given alone did not affect the morphine-produced CPP, nor did it affect the baseline place preference in rats treated with saline vehicle (FIG. 3).

Discussion of the Results

(−)-Morphine, But Not Dextro-morphine, Produces CPP Given Subcutaneously

Previous studies have demonstrated that μ-opioid agonists such as (−)-morphine, D-Ala$^2$-N-MePhe$^4$-Gly$^5$-ol-enkephalin or endomorphin-1 given systemically or intracerebroventricularly in mice or rats produce CPP (Wu et al., (2004) *Neurosci. Lett.* 356, 157-161). The results of the studies described here are consistent with previous findings that (−)-morphine given subcutaneously dose-dependently produced CPP. The CPP produced by (−)-morphine is blocked by p-opioid receptor antagonist naltrexone or naloxonazine, indicating that the effect is mediated by the stimulation of μ-opioid receptors (Olmstead and Burns, (2005) *Psychopharmacology* 12:1-6).

Unlike naturally occurring morphine alkaloid, the synthetic dextro-morphine does not have any affinity and efficacy for μ-opioid receptors and therefore does not produce analgesia and other m-opioid receptor mediated effects (Jacquet et al., 1977). In the studies described here it was found that dextro-morphine at a dose 3 μg/kg given systemically did not produce CPP nor conditioned place aversion. The finding is consistent with previous findings by Mucha and Herz (1986) that dextro-morphine at a dose of 4 mg/kg given systemically does not produce any CPP or conditioned place aversion. (−)-Morphine at the same dose, on the other hand, produces CPP. These findings are consistent with the view that dextro-morphine does not interact with the μ-opioid receptors and does not produce CPP or conditioned place aversion (Jacquet et al., 1977; Mucha and Herz, 1986). Thus, the CPP produced by morphine is stereospecific; it is only produced by the opioid receptor active isomers, such as levorotatory (−)-morphine, but not dextrorotatory dextro-morphine.

(+)-Morphine at a Dose Range 0.1-100 μg/kg Given Systemically Produce a U-shaped Dose-response Curve in Attenuating the Morphine-produced CPP In the studies described here it was found that (+)-morphine at a dose range of 0.1-3 μg/kg dose-dependently attenuated the (−)-morphine-produced CPP. Paradoxically, (+)-morphine at a higher dose 100 μg/kg was ineffective in attenuating the (−)-morphine-produced CPP. Thus, (+)-morphine at a dose range from 0.1 to 100 μg/kg induces a U-shaped dose-response curve with a maximal attenuation at a dose of 3 μg/kg for attenuating the (−)-morphine-produced CPP. The results of the present study indicate that (+)-morphine can be developed as an antidote for the treatment of opiate addiction. The therapeutic window of the dose of (+)-morphine for the anti-addiction therapy should be in the μg/kg dose range. Higher doses of (+)-morphine would not be effective in providing the therapeutic effect.

The U-shaped dose-response curve is also known as hormesis (Calabrese and Baldwin, (2003) *Annu. Rev. Pharmacol. Toxicol.* 43, 175-197). A well-documented example of a U-shaped dose-response relationship concerns the actions of corticosteroid hormones in the CA1 area of the hippocampus (Joëls, (2006) *Trends Pharmacol. Sci.* 27, 244-250), a brain region that is important for learning and memory formation. The neurosteroids have been proposed to be the endogenous ligand for sigma-1 receptors in the central nervous system (Monnet and Maurice, 2006). In a modified passive-avoidance learning task in mice, pre-training or post-training administration of neurosteroids, pregnenolone sulfate or dehydroepiandrosterone sulfate enhances memory retention of passive-avoidance training. In both treatments, an inverted U-shaped dose-response curve is obtained covering 2- to 5-fold dose range in a manner typical for memory-enhancing substance. The neurosteroid-induced facilitation of memory retention may involve central sigma receptors, because the effect of neurosteroids is completely antagonized by sigma receptor antagonist haloperidol (Reddy and Kulkarni, (1998) *Brain Res.* 791, 108-116). It is postulated that dextro-morphine mimics the effect of endogenous neurosteroids to stimulate the sigma receptors for producing the anti-CPP (see details in the next section below). The U-shaped dose-response curve for dextro-morphine to attenuate the (−)-morphine CPP is consistent with this hypothesis.

The Attenuation of the (−)-morphine-produced CPP by (+)-morphine Is Mediated by the Sigma Receptor Activation Most of dextrorotatory opiates such as (+)-pentazocine and (+)-N-allyl-normetazocine ((+)-SKF10047) exhibit the sigma receptor binding activity (Walker et al., (1992) *Brain Res.* 581, 33-38). It is therefore reasonably believed that (+)-morphine acts on sigma receptors to produce the anti-CPP effect. BD1047 is a selective sigma receptor antagonist (McCracken et al., (1999) *Eur. J. Pharmacol.* 370, 225-232). BD1047 was then used to determine if the blockade of the sigma receptors by BD1047 pretreatment would reverse the attenuation of the (−)-morphine-produced CPP induced by (+)-morphine. It was found in the present study that pretreatment with BD1047 dose-dependently reversed the attenuation of the (−)-morphine-produced CPP induced by (+)-morphine, indicating that sigma receptors are involved in (+)-morphine-induced anti-CPP effects. The sigma receptor stimulatory property of (+)-morphine can also be found in our other studies of the antianalgesic effect of (+)-morphine. Pretreatment with (+)-morphine attenuates the (−)-morphine-produced analgesia (Wu et al., 2005). The attenuation of the (−)-morphine-produced analgesia was blocked by the pretreatment of the BD1047 (unpublished observation). The results of these studies clearly indicate that (+)-morphine exerts its pharmacologoical effects via the sigma receptor activation.

The recent demonstration by Romieu (2003) *Neurosci.* 23, 3572-3576, that neurosteroids, endogenous ligands for sigma-1 receptors, are able to modulate the acquisition of the cocaine-induced CPP suggest their influence on acquisition of drug addiction. Neurosteroids pregnenolone and dehydroxypregnolone potentiates the cocaine-induced CPP acquisition, as do selective sigma-1 receptor agonists, like igmesine or PRE-084, and the effect is blocked by the sigma-1 receptor antagonist BD1047. Selective sigma-1 receptor antagonist, like BD1047 or NE100, or antisense oligodeoxynucleotide probe targeting the sigma-1 receptor also blocks acquisition or expression of the cocaine-induced CPP in mice. Similar observations could be presented for abuse of amphetamine and alcohol, which also involve sigma receptor activation. The activation of sigma-1 receptors by sigma-1 receptor agonist SA4503 (1-(3,4-dimethoxyphenethyl)-4-(phenylpropyl)pipperazine) attenuates the acquisition of the CPP produced by nicotine. These observations clearly indicate that sigma-1 receptors are involved in the CPP produced by cocaine, amphetamine, alcohol and nicotine as well.

Based on the results of Examples 1 through 3, it was concluded that (+)-morphine at a μg/kg dose range given systemically attenuates the morphine-produced CPP. The blockade of the sigma receptor by BD1047 reverses the attenuation of (−)-morphine-produced CPP induced by (+)-morphine, indicating that the (+)-morphine-induced anti-CPP is mediated by sigma receptor activation.

Example 4

Figure 4:
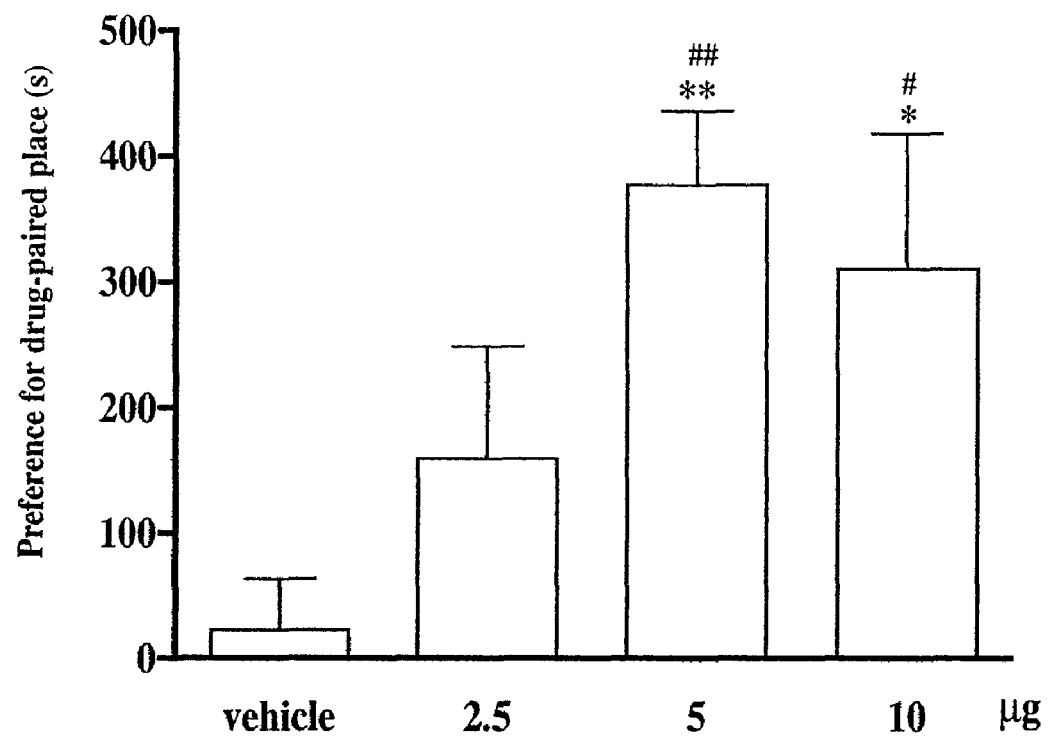
FIG. 4 shows that (−)-morphine microinjected into the nucleus accumbens (Acb) shell dose-dependently produces the conditioned place preference. After completion of the pre-conditioning measurement on the $1^{st}$ day, groups of rats were place conditioned after microinjection with different doses of (−)-morphine (2.5, 5 or 10 µg) or vehicle given into the Acb shell twice a day for three days and the post-conditioning was measured on the $5^{th}$ day. Each column represents the mean of the conditioned place preference score and the vertical bar represents the S.E.M.; n=7-13. Paired t test was used to compare production of conditioned place preference of individual dose; for the group of rats microinjected with 2.5, 5 or 10 µg of (−)-morphine or vehicle, t=1.8, 6.4, 2.9 and 0.04 and df=7, 9, 6 and 6, respectively, #P<0.01, ##P<0.001. One-way ANOVA followed by Dunnett's post-test was used to test difference between groups, $F_{(3, 34)}=6.12$; *P<0.05, **P<0.01.

Effect of (−)-morphine Microinjected into the Acb Shell on the Production of the Conditioned Place Preference Groups of rats were microinjected with different doses of (−)-morphine or vehicle given into the Acb shell for place conditioning repeated for three days. (−)-Morphine at a dose of 2.5 or 5 μg given into the Acb shell dose-dependently produced conditioned place preference and at a higher dose of 10 μg, it produced no further increase of conditioned place preference (FIG. 4). Microinjection of the vehicle did not affect the baseline place conditioning response. Five μg of (−)-morphine was then used for place conditioning in the following experiments.

Example 5

Figure 5:
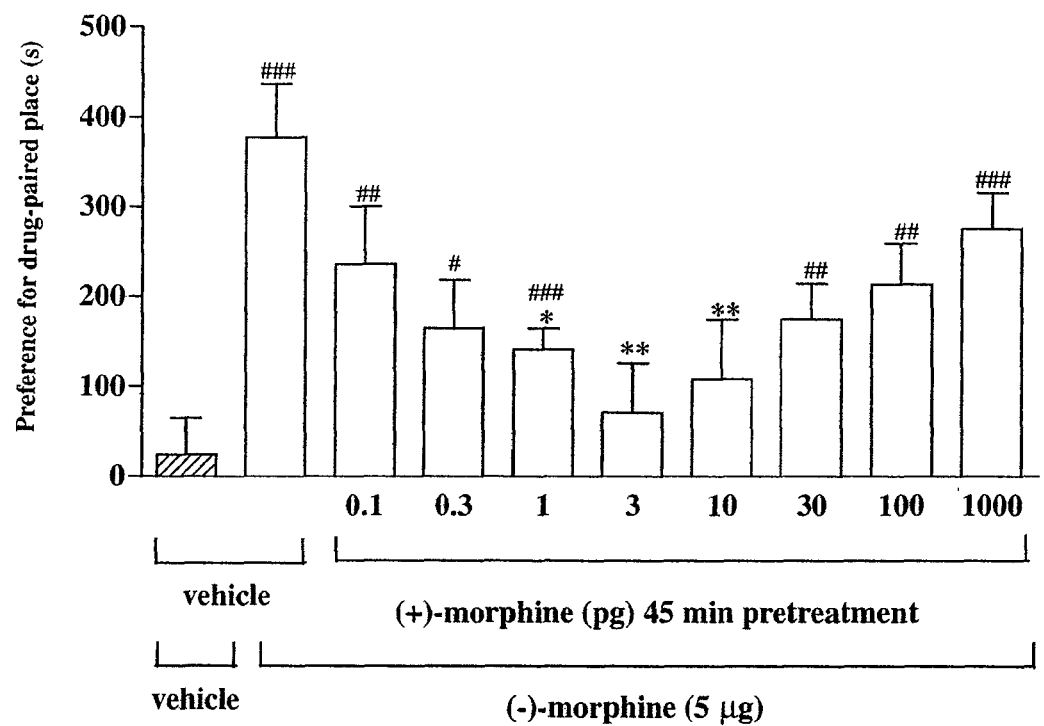
FIG. 5 shows that the (+)-morphine pretreatment given into the Acb shell attenuates the conditioned place preference produced by (−)-morphine from the Acb shell. After completion of the pre-conditioning measurement on the $1^{st}$ day, groups of rats were pretreated with different doses (0.1 to 1000 pg) of (+)-morphine or vehicle for 45 min and were place conditioned after microinjection of (−)-morphine (5 µg) or vehicle given into the Acb shell twice a day for three days. The post-conditioning was measured on the $5^{th}$ day. Each column represents the mean of conditioned place preference score and the vertical bar represents the S.E.M.; n=6-17; Paired t test was used to compare production of the conditioned place preference of individual dose: For the group of rats pretreated with vehicle followed by vehicle or (−)-morphine challenge, t=0.6 and 6.4 and df=12 and 9, respectively. For the group of the rats pretreated with different dose of (+)-morphine (0.1, 0.3, 1, 3, 10, 30, 100 or 1000 pg) followed by (−)-morphine challenge, t=3.7, 2.9, 6.4, 0.8, 0.7, 4.4, 4.2 and 7.2 and df=7, 5, 8, 6, 12, 5, 12 and 17, respectively. #P<0.05, ##P<0.01, ###P<0.001. One-way ANOVA followed by Dunnett's post-test was used to test difference between groups, $F_{(8, 91)}=3.02$; *P<0.05, **P<0.01.
Figure 6:
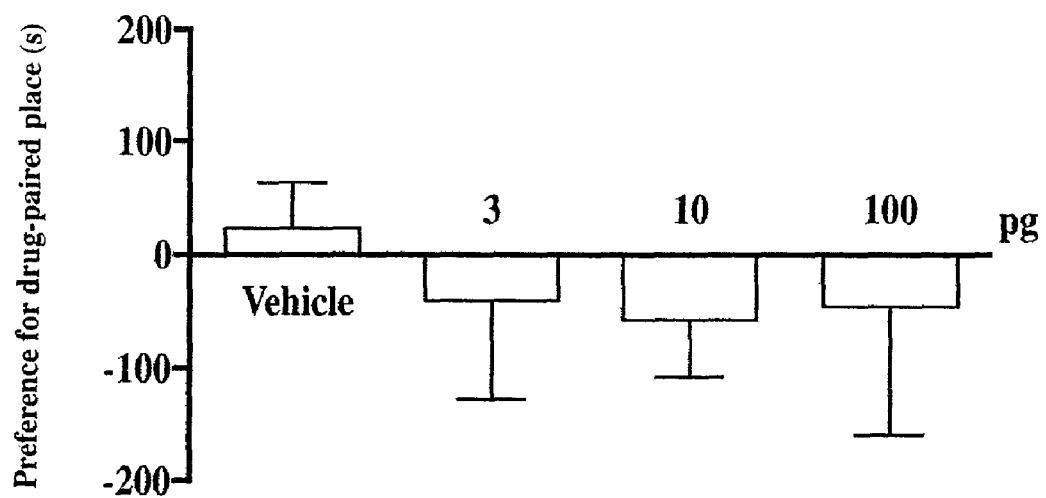
FIG. 6 shows that (+)-morphine microinjected into the Acb shell does not have any effect on the conditioned place preference. After completion of the pre-conditioning measurement on the $1^{st}$ day, groups of rats were place conditioned after microinjection with different doses of (+)-morphine (3, 10 or 100 pg) or vehicle into the Acb shell twice a day for three days. The post-conditioning was measured on the $5^{th}$ day. Each column represents the mean of the conditioned place preference score and the vertical bar represents the S.E.M.; n=7-13 rats. Paired t test was used to compare production of conditioned place preference of individual dose: For the group of rats microinjected with vehicle or 3, 10 or 100 pg of (+)-morphine, t=0.6, 1.7, 1.8 and 1.5 df=12, 7, 7 and 9, respectively. One-way ANOVA followed by Dunnett's post-test was used to test difference between groups; $F_{(3, 34)}=0.267$.
Figure 7:
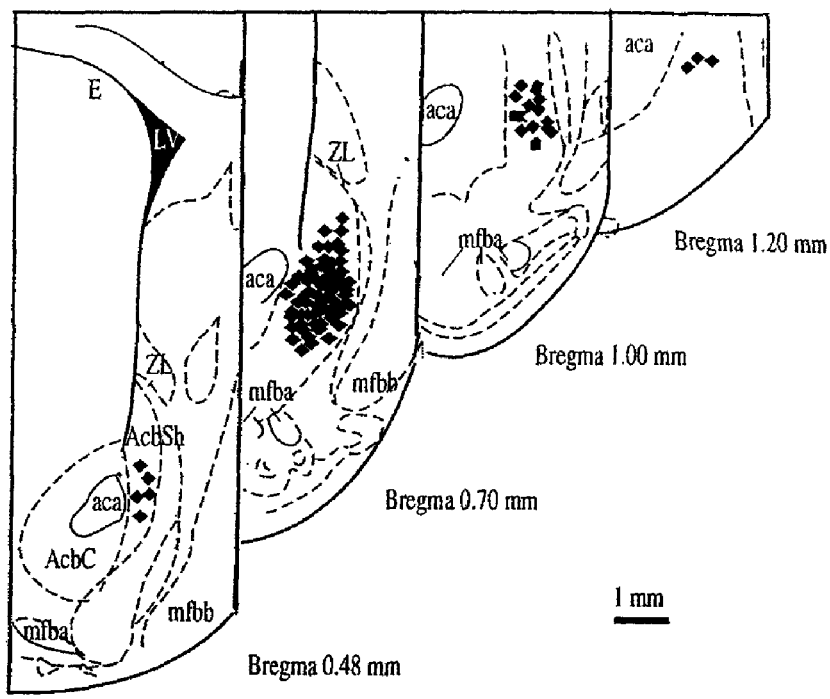
FIG. 7 shows the injection sites for drug or vehicle at the Acb shell for experiments shown in FIG. 4 through FIG. 6, marked in the coronal sections of the atlas of Paxinos and Watson (1997) "The rat brain in stereotaxic coordinates", Academic Press, San Diego.

Effects of (+)-morphine Microinjected into the Acb Shell on the (−)-morphine-produced Conditioned Place Preference Groups of rats were pretreated in the home cage with different doses (0.1 to 1000 pg) of (+)-morphine or saline vehicle given into the Acb shell for 45 min before microinjection of (−)-morphine (5 μg) given into the same site for place conditioning repeated for three days. Pretreatment with (+)-morphine at a dose from 0.1 to 10 pg dose-dependently attenuated the (−)-morphine-produced conditioned place preference. However, (+)-morphine at a higher dose of 30, 100, and 1000 pg did not attenuate the (+)-morphine-produced conditioned place preference (FIG. 5). Thus, (+)-morphine produced a U-shape of the dose-response curve with a maximal inhibition at 3 pg. (+)-Morphine (3 to 100 pg) microinjected into the Acb shell given alone did not produce any conditioned place preference in rats (FIG. 6). Histological examination verified that all the injection sites for (+)-morphine and/or (−)-morphine intended for the Acb shell were within the intended region of the brain site (FIG. 7).

Example 6

Microinjection of Endomorphin-1 into the VTA Increases the Release of Dopamine from Nucleus Accumbens Shell and the Increased Release of Dopamine is Blocked by (−)-naloxone Pretreatment Given into the VTA in Urethane-anesthetized Rats Groups of rats were microinjected with a various dose of endomorphin-1 (1, 3 and 10 μg) or vehicle given into the VTA and the release of dopamine from the Acb shell were studied. Endomorphin-1 at a dose of 10 μg, but not 1 or 3 μg, caused an increase of the extracellular dopamine in the Acb shell 15 min after injection given into the VTA. The dopamine level returned to baseline 60 min thereafter (FIG. 8A). To determine if the increased release of dopamine induced by endomorphin-1 is mediated by the stimulation of μ-opioid receptors, the effect of (−)-naloxone on the increased release of dopamine induced by endomorphin-1 was then studied. Co-administration with (−)-naloxone at a dose 40 ng, but not 4 ng, for 45 min attenuated the increase of the extracellular dopamine in the Acb shell induced by endomorphin-1 from the VTA (FIG. 8B).

Example 7

Figure 9:
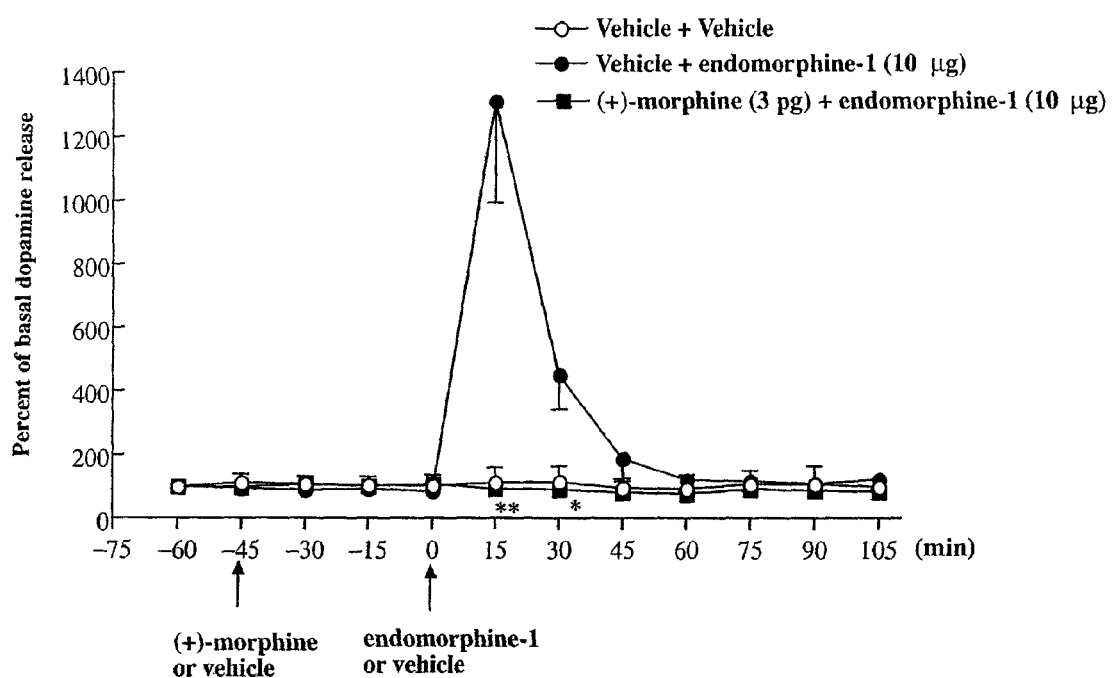
FIG. 9 shows that the increase of the extracellular dopamine release at the nucleus accumbens shell induced by endomorphin-1 microinjected into the VTA is blocked by (+)-morphine in rats. Groups of rats were microinjected with (+)-morphine (3 pg) or vehicle into the VTA 45 min before endomorphin-1 (10 μg) was microinjected into the VTA. The perfusates from the microdialysis probe at the nucleus accumbens shell were collected every 15 min from 15 min before first microinjection and continuously collected for another 105 min after last microinjection. The perfusates were then analyzed their dopamine level. Each point represents the percent basal dopamine release and the vertical bar represents the S.E.M.; n=3-9. Two-way ANOVA followed by Bonferroni post-test was used to test the difference between groups. For the groups of the rats injected with (+)-morphine and endomorphin-1 versus vehicle and endomorphin-1, $F_{interaction\ (7,\ 80)}=11.47$, $F_{treatment\ (1,\ 80)}=26.03$, $F_{time\ (7,\ 80)}=11.58$, *P<0.05, **P<0.005; only the data of the dopamine level after the 0 min time point were used for statistic analysis; the vehicle pretreatment followed by vehicle microinjected group was not included in the statistic analysis.

(+)-Morphine Pretreatment Blocks the Increase of the Extracellular Dopamine in the Acb Shell Induced by Endomorphin-1 from the VTA To determine if the increase of the extracellular dopamine produced by the stimulation of μ-opioid receptors from the VTA can be blocked by (+)-morphine, the effect of (+)-morphine on the increased release of dopamine induced by endomorphin-1 was then studied. Pretreatment with (+)-morphine (3 pg) given into the VTA for 45 min completely blocked the increase of the extracellular dopamine in the Acb shell produced by endomorphin-1 (FIG. 9). Microinjection of (+)- morphine given into the VTA did not affect the basal levels of extracellular dopamine in the Acb shell.

Discussion of the Results (−)-Morphine, but not (+)-morphine, Given into the Mesolimbic Nucleus Accumbens Produces the Conditioned Place Preference Unlike naturally occurring (−)-morphine, which produces analgesia and other μ-opioid receptor mediated pharmacological effects, the synthetic (+)-morphine does not have any affinity and efficacy for μ-opioid receptors and therefore does not produce analgesia and other effects mediated by the stimulation of μ-opioid receptors (Jacquet et al., 1977). Applicant previously demonstrated that only (−)-morphine, but not (+)-morphine, given systemically produces the conditioned place preference in rats. The finding is consistent with previous findings by Mucha and Herz (1986) that (+)-morphine (4 mg/kg) given systemically does not produce any conditioned place preference or conditioned place aversion. (−)-Morphine at the same dose, on the other hand, produces the conditioned place preference. Thus, the conditioned place preference produced by morphine is stereospecific; it is only produced by the opioid receptor active isomers, such as levorotatory (−)-morphine, but not dextrorotatory (+)-morphine.

The VTA and nucleus accumbens represent two key structures of the mesolimbic dopaminergic system in the CNS for the reinforcing properties of opiates. The microinjection technique was then used to deliver (−)-morphine or (+)-morphine into the Acb shell and the conditioned place preference produced by (−)-morphine or (+)-morphine given into the same Acb shell was then measured. It was found in the present study that only (−)-morphine, but not (+)-morphine delivered into nucleus accumbens shell produced the conditioned place preference (FIGS. 4 and 6). The conditioned place preference produced by (−)-morphine is blocked by co-administration with μ-opioid receptor antagonist naltrexone, indicating that the effect is mediated by the stimulation of μ-opioid receptors.

(+)-Morphine at an Extremely Low Picogram Dose Given into the Mesolimbic Acb Shell Attenuates the (−)-morphine-produced Conditioned Place Preference It was found in the present study that (+)-morphine at an extremely low picogram dose attenuated the conditioned place preference produced by (−)-morphine. Paradoxically, a higher dose of (+)-morphine was ineffective in attenuating (−)-morphine-produced conditioned place preference (FIG. 5.). Thus, (+)-morphine produced a U-shape dose-response curve with a maximal attenuation at a dose of 3 pg. Similarly, (+)-morphine given systemically also produces a U-shaped dose-response curve in attenuating the (−)-morphine-produced conditioned place preference.

The U-shaped dose-response curve is also known as hormesis (Calabrese and Baldwin, 2003). A well-documented example of a U-shaped dose-response relationship concerns the actions of corticosteroid hormones in the CA1 area of the hippocampus, a brain region that is important for learning and memory formation. The neurosteroids have been proposed to be the endogenous ligand for sigma-1 receptors in the central nervous system. In a modified passive-avoidance learning task in mice, pretraining or posttraining administration of neurosteroids, pregnenolone sulfate or dehydroepiandrosterone sulfate enhances memory retention of passive-avoidance training. In both treatments, an inverted U-shaped dose-response curve is obtained covering 2- to 5-fold dose range in a manner typical for memory-enhancing substance. The neurosteroid-induced facilitation of memory retention may involve central sigma receptors, because the effect of neurosteroids is completely antagonized by sigma receptor antagonist haloperidol. It is postulated that (+)-morphine may mimic the effect of endogenous neurosteroids to stimulate the sigma receptors for producing the anti-addictive effect (see details in the next paragraph below). The U-shaped dose-response curve for (+)-morphine to attenuate the (−)-morphine conditioned place preference is consistent with this hypothesis.

It is hypothesized that (+)-morphine attenuates the (−)-morphine-produced conditioned place preference via the activation of the naloxone-sensitive sigma receptor. The hypothesis is supported by our previous findings that the attenuation of the (−)-morphine-produced conditioned place preference induced by (+)-morphine was reversed by the pretreatment with the sigma receptor antagonist BD1047. Applicant previously demonstrated that (+)-morphine pretreated systemically or given into periaqueductal gray attenuates the antinociception produced by (−)-morphine given systemically. The attenuation of the (−)-morphine-produced antinociception is blocked or reversed by the sigma receptor antagonist BD1047 and by the (+)-naloxone or (−)-naloxone pretreatment, indicating that the anti-morphine effects of (+)-morphine are mediated by the activation of the naloxone-sensitive sigma receptor.

Figure 8:
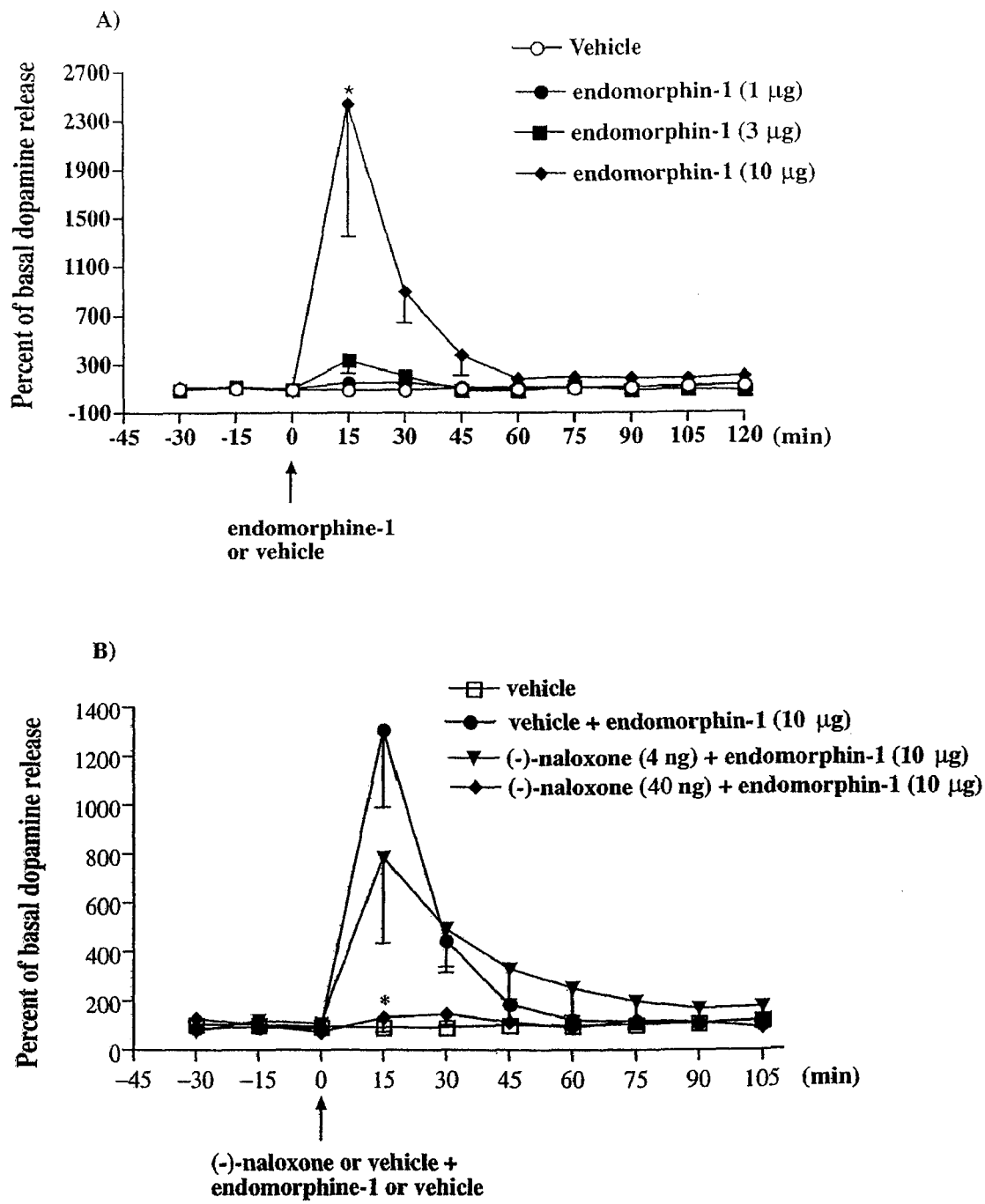
FIGS. 8A-B shows that endomorphin-1 given into the ventral tegmental area (VTA) increases the extracellular dopamine in the Acb (A) and the increase of the extracellular dopamine in the Acb by endomorphin-1 was blocked by (−)-naloxone given into the VTA (B). Groups of rats were microinjected with endomorphin-1 (1, 3 or 10 μg) or vehicle into the VTA (A). In other groups of rats, (−)-naloxone (4 or 40 ng) or vehicle was co-microinjected into the VTA with endomorphin-1 (10 μg). The perfusates from the microdialysis probe at the nucleus accumbens shell were collected every 15 min from 30 min before microinjection and continuously collected for another 120 min (A) or 105 min (B) after microinjection. The perfusates were then analyzed their dopamine level. Each point represents the percent basal dopamine release and the vertical bar represents the S.E.M.; n=3-9. Two-way ANOVA followed by Bonferroni post-test was used to test the difference between groups; (A) For the groups of the rats injected with different dose of endomorphin-1 versus vehicle $F_{interaction\ (24,\ 189)}=1.573$, $F_{treatment\ (3,\ 189)}=4.44$, $F_{time\ (8,\ 189)}=2.14$ 1, *P<0.005. (B) For the group of rats injected with different dose of (−)-naloxone+endomorphin-1 versus vehicle+endomorphin-1, $F_{interaction\ (18,\ 150)}=3.338$, $F_{treatment\ (2,\ 150)}=7.671$, $F_{time\ (9,\ 150)}=11.17$, *P<0.01; only the data of the dopamine level after the 0 min time point were used for the statistic analysis; the group of rats microinjected with vehicle alone in (B) was not included in the statistic analysis.

Dextro-morphine Attenuates the Increase of the Extracellular Dopamine in the Nucleus Accumbens Shell Produced by μ-opioid Agonist Endomorphin-1 from the VTA It was found in the present study that endomorphin-1 given into the VTA caused the increase of the extracellular dopamine in the Acb shell. The increase of the extracellular dopamine in the Acb shell by the endomorphin-1 is blocked by (−)-naloxone pretreatment, indicating that the effect is mediated by the μ-opioid receptor activation (FIG. 8). Thus, stimulation of μ-opioid receptors by (−)-morphine or other μ-opioids in the VTA enhances mesolimbic dopaminergic neurotransmission, presumably by inhibition of GABAergic interneurons, thereby disinhibiting mesolimbic dopaminergic neurons and increasing both somatodendritic and axonal dopamine release. An increase in the extracellular dopamine in the nucleus accumbens has been reported by systemic (−)-morphine and by intracerebroventricular injection of the μ-receptor agonist, D-Ala$^2$-N-MePhe$^4$-Gly-ol$^5$]enkephalin. It was found in the present study that the increased release of dopamine in the Acb induced by the μ-opioid receptor agonist endomorphin-1 was blocked by the (+)-morphine given into the VTA (FIG. 9). Thus, the behavioral response to (+)-morphine in attenuating the (−)-morphine-produced conditioned place preference is correlated with the biochemical finding that (+)-morphine blocks the increase of extracellular dopamine in the Acb elicited by the specific μ-opioid receptor agonist endomorphin-1 from the VTA. The finding supports the hypothesis that (+)-morphine, which activates naloxone-sensitive sigma receptors, inhibits the (−)-morphine-produced conditioned place preference by attenuating the increase of extracellular dopamine in the mesolimbic VTA-nucleus accumbens system.

The results of the present study indicate that (+)-morphine can be used for the treatment of opiate addiction. The therapeutic window of the dose of (+)-morphine for the anti-addiction therapy should be in the picogram dose range. Higher doses of (+)-morphine are not effective in providing the therapeutic effect.

Example 8

Figure 10:
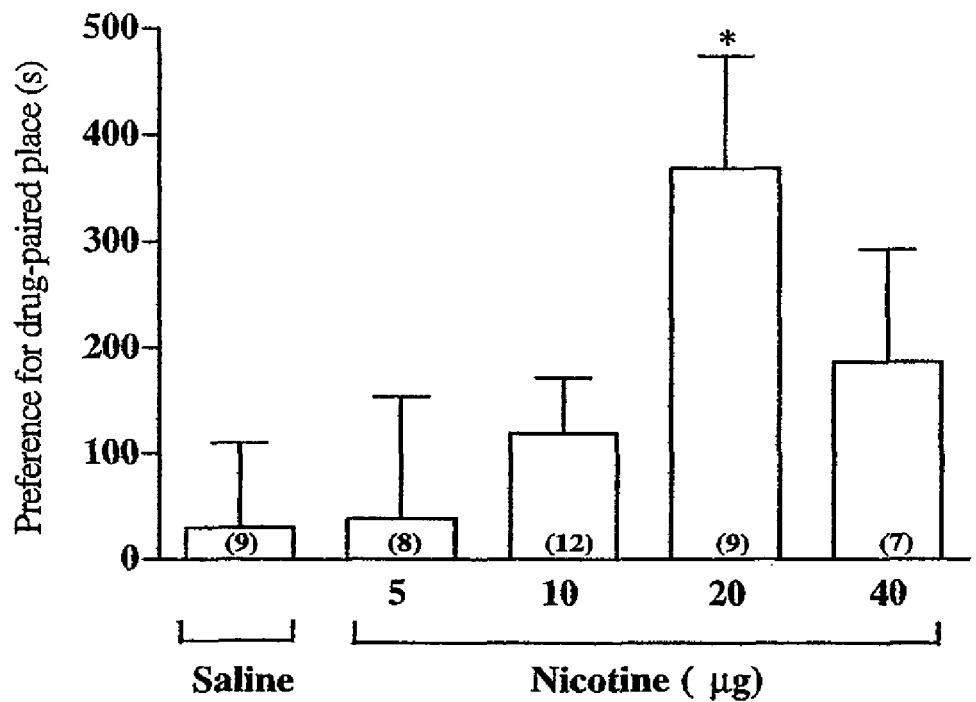
FIG. 10 shows that nicotine microinjected into the posterior Acb shell dose-dependently produces the conditioned place preference. After completion of the pre-conditioning measurement on the 1st day, groups of rats were place conditioned after microinjection with different doses of nicotine (5, 10, 20 or 40 μg) or vehicle given into the Acb shell twice a day for three days and the post-conditioning was measured on the 5th day. Each column represents the mean of the conditioned place preference score and the vertical bar represents the S.E.M.; Number in the parenthsis indicates the number of rats used; One-way ANOVA followed by Dunnett's post-test, F (4,40)=2.394, *P<0.05.
Figure 11:
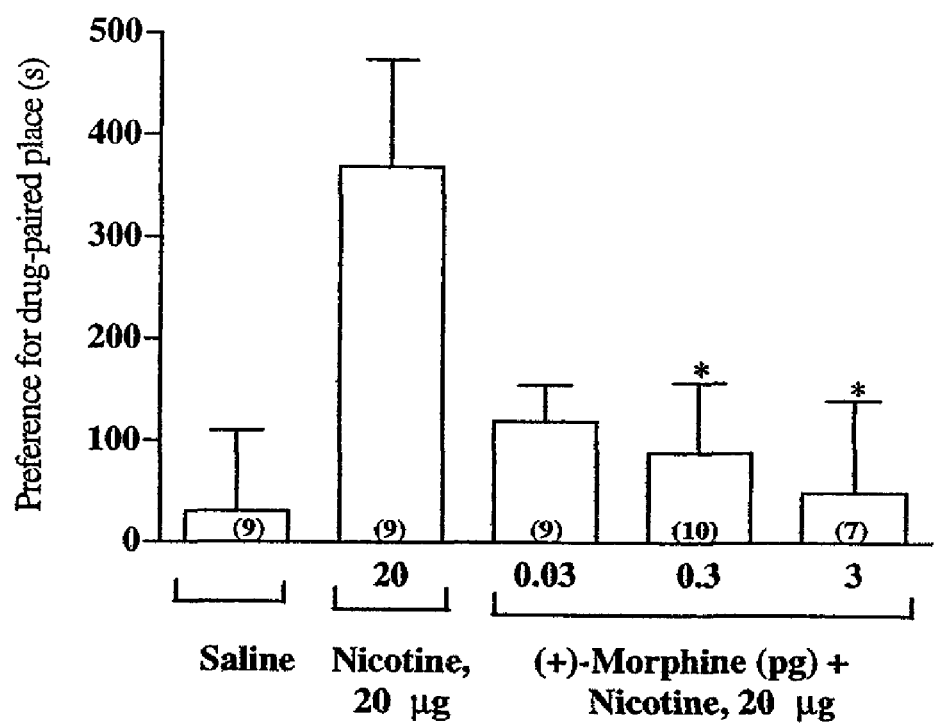
FIG. 11 shows that (+)-morphine pretreatment given into the Acb shell attenuates the conditioned place preference produced by nicotine from the Acb shell. After completion of the pre-conditioning measurement on the 1st day, groups of rats were pretreated with different doses (0.03, 0.3 or 3 pg) of (+)-morphine or vehicle for 45 min and were place conditioned after microinjection of nicotine (20 μg) or vehicle given into the Acb shell twice a day for three days. The post-conditioning was measured on the 5th day. Each column represents the mean of conditioned place preference score and the vertical bar represents the S.E.M.; Number in the parenthesis indicates the number of the rats used; One-way ANOVA followed by Dunnett's post-test. F (3,31)=3.115, *P<0.05. Saline group serves as control, which does not include in the statistical analysis.

Blocking Effect of (+)-morphine on Nicotine-produced Conditioned Place Preference from Acb Nicotine at a dose from 5 to 20 μg microinjected into the Acb dose-dependently increased the conditioned place preference. However, a higher of dose of nicotine 40 μg produced less increase of the conditioned place preference than that of 20 μg of nicotine (FIG. 10). The increase of the conditioned place preference caused by nicotine (20 μg) given into the Acb was blocked dose-dependently by the pretreatment of (+)-morphine (0.03 to 3 pg) given into the Acb. (+)-Morphine at a dose of 0.3 pg was found to completely block the nicotine-produced increase of the conditioned place preference (FIG. 11). Thus, (+)-morphine blocks the increase of the conditioned place preference from the Acb. (+)-Morphine can be used clinically for the treatment of addiction to tobacco smoking.

Discussion of the Results

To determine whether the dopaminergic reward system is modulated by nicotine, a microinjection technique was used to facilitate the identification of specific brain areas involved in the reinforcing properties of nicotine. Much evidence suggests that nicotine-induced dopamine release in the mesolimbic reinforcement pathway is associated with nicotine addition (Bonci, A. (2003) *Trends in pharmacological Sciences*, vol. 24: 4, page 172-177; Balfour et al., (2000) The putative role of extrasynaptic mesolimbic dopamine in the neurobiology of nicotine dependence. *Behav Brain Res* 113:73-83; and Corrigall W A and Coen K M (1991) Selective dopamine antagonists reduce nicotine self-administration. *Psychopharmacology* 104:171-176). The VTA (ventral tegmental area), Acb (posterior nucleus accumbens) and medial frontal cortex (MFC) represent key structure of the mesolimbic dopamine system.

The dopamine perikarya are located in VTA, while the Acb and MFC represent important terminal fields of the fibers arising therein. Nicotine preferentially increases the firing rate of dopamine neurons in the VTA. This activation is mainly mediated by β2nAChRs. A single systemic injection of nicotine elevates dopamine in the Acb for hours. This prolonged dopamine signal is sustained, in part, because there is a wide range of response by the dopamine neurons. Intra-Acb or intra-VTA administration of nicotine elicits an acute increase in extracellular dopamine levels in Acb. The nicotine-induced increases of dopamine in the Acb are in part mediated by dopamine neurons in the VTA. A reduction of dopamine content at Acb after termination of nicotine infusion or during mecamylamine-precipitated abstinence is observed but not in prefrontal cortex. These observations suggest that rewarding effects are associated with the activation of dopamine neurons in VTA and then affect the dopamine release in the Acb.

Both (−)-morphine and nicotine produce CPP. A cross-tolerance between morphine- and nicotine-induced conditioned place preference (CPP) in mice has been reported, suggesting that both CPPs induced by (−)-morphine and nicotine share the same mesolimbic dopaminergic pathways. Nicotine receptor stimulation induces the release of endogenous opioid peptides, such as β-endorphin and enkephalins. The mu-opioid receptor is central to the development of drug addiction. (See, Contet, C. (2004) *Current Opinion in Neurobiology* 14:370-378). It is described here that nicotine releases endogenous opioid peptides and indirectly modulates the mu-opioid receptor function for producing addiction. These observations suggest that the behavioral CPP induced by nicotine is mediated by the increased release of endogenous opioid peptides and the μ-opioid receptor activation in the dopaminegic mesolimbic system. Therefore, as described herein (+)-Morphine is expected to block nicotine-induced increase of dopamine and CPP.

Example 9

Figure 12:
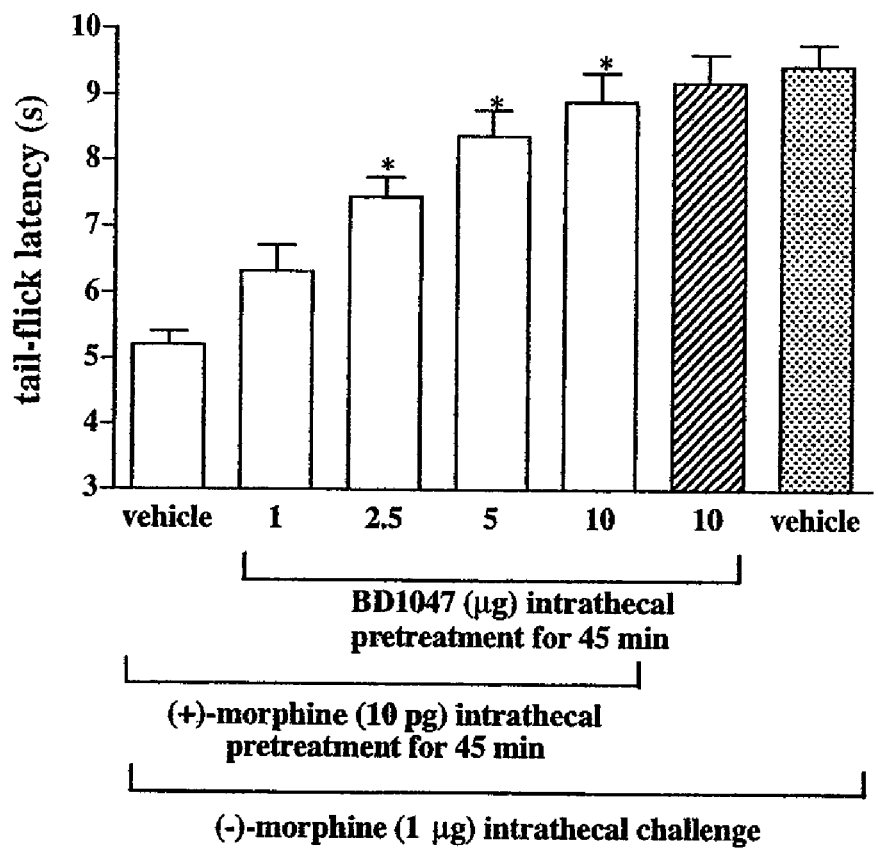
FIG. 12 shows that pretreatment with the sigma receptor antagonist BD1047 reverses the attenuation of the (−)-morphine-produced tail-flick inhibition induced by (+)-morphine in the mouse spinal cord. Groups of mice were co-administered with different doses (1-10 μg) of BD1047 and (+)-morphine (10 pg) 45 min before (−)-morphine (1 μg) given intrathecally. The tail-flick responses were measured 15 min after last injection. Each column represents the mean and the vertical bar represents the S.E.M. with 8 to 9 mice in each group. The first two columns from the right represented control groups, which did not include in the statistic analysis. One-way ANOVA followed by Dunnett's post-test was used to test the difference between groups; the F (4,37)=17.27; *P<0.01 compared with the vehicle injected group (the first column from the left).
Figure 13:
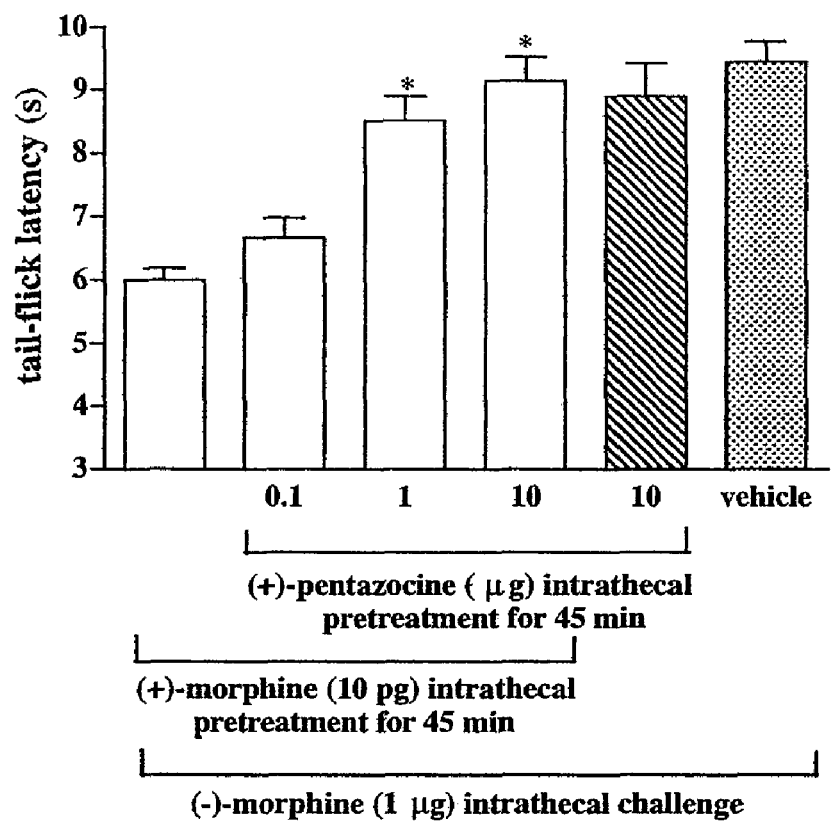
FIG. 13 shows that pretreatment with the naloxone-sensitive sigma receptor ligand (+)-pentazocine reverses the attenuation of the (−)-morphine-produced tail-flick inhibition induced by (+)-morphine in the mouse spinal cord. Groups of mice were co-administered with different doses (0.1-10 μg) of (+)-pentazocine and (+)-morphine (10 pg) 45 min before (−)-morphine (1 μg) given intrathecally. The tail-flick responses were measured 15 min after last injection. Each column represents the mean and the vertical bar represents the S.E.M. with 8 to 9 mice in each group. The first two columns from the right represented control groups, which did not include in the statistic analysis. One-way ANOVA followed by Dunnett's post-test was used to test the difference between groups; the F (3,32)=20.72; *P<0.01 compared with the vehicle injected group (the first column from the left).

Effect of BD1047 or (+)-pentazocine Pretreatment on the Attenuation of the (−)-morphine-produced Tail-flick Inhibition Induced by (+)-morphine The sigma receptor ligands BD1047 and (+)-pentazocine were used to determine if the non-opioid naloxone-sensitive sigma receptor mechanism is involved in mediating the (+)-morphine-induced antianalgesia in the mouse spinal cord. Different groups of mice were pretreated intrathecally with (+)-morphine (10 pg) and different doses of BD1047 (1-10 μg) or (+)-pentazocine (0.1-10 μg) (Mei and Pasternak, 2002) for 45 min (Wu et al., 2005) before intrathecal injection of (−)-morphine (1 μg) and the tail-flick response was measured 15 min after the (−)-morphine challenge. Intrathecal pretreatment with (+)-morphine (10 pg) attenuated the (−)-morphine-produced tail-flick inhibition. The attenuation of the (−)-morphine-produced tail-flick inhibition by (+)-morphine was reversed by BD1047 (FIG. 12) or (+)-pentazocine pretreatment (FIG. 13) in a dose-dependent manner. Intrathecal pretreatment with BD1047 (10 μg) or (+)-pentazocine (10 μg) given alone 45 min prior to intrathecal injection of (−)-morphine (1 μg) did not affect the (−)-morphine-produced tail-flick inhibition (9.19±0.42 s and 8.89±0.53 s, respectively) (FIGS. 12 and 13).

Discussion of the Results (+)-Morphine Attenuates the (−)-morphine-produced Antinociception Via the Activation of the Naloxone-sensitive Sigma Receptor in the Mouse Spinal Cord Applicants previously demonstrated that (+)-morphine pretreated systemically attenuates the antinociception produced by (−)-morphine given systemically. The attenuation of the systemic (−)-morphine-produced antinociception was blocked or reversed by the sigma receptor antagonist BD1047 and by the (+)-naloxone or (−)-naloxone pretreatment, indicating that the antianalgesic action of (+)-morphine given systemically against systemic (−)-morphine-produced antinociception is mediated by the activation of the naloxone-sensitive sigma receptor (Wu et al., 2007). The present study was then undertaken to determine if the antianalgesic action of (+)-morphine given spinally is also mediated by the naloxone-sensitive sigma receptors. It was found in the present study that pretreatment with the sigma receptor antagonist BD1047 given intrathecally blocked or reversed the attenuation of the antinociception produced by (−)-morphine given intrathecally. Applicants previously reported that the attenuation of the intrathecal (−)-morphine-produced antinociception induced by (+)-morphine given intrathecally is blocked or reversed by (+)-naloxone or (−)-naloxone given intrathecally (Wu et al., 2005). Applicant also previously demonstrated that the antianalgesia of (+)-morphine from the supraspinal ventral periaqueductal gray is mediated by the naloxone-sensitive sigma receptor. These findings indicate that the antianalgesia induced by (+)-morphine against antinociception produced by (−)-morphine is mediated by the activation of the naloxone-sensitive sigma receptor in both spinal cord and supraspspinal sites.

(+)-Pentazocine is a selective sigma receptor ligand, which acts on both the naloxone-inaccessible sigma receptors and naloxone-sensitive sigma receptor. Applicants also previously demonstrated that systemic administration of (+)-pentazocine attenuates the antinociception produced by (−)-morphine given systemically. The attenuation of the (−)-morphine-produced antinociception induced by (+)-pentazocine is blocked by the BD1047 and (+)-naloxone, indicating that that (+)-pentazocine given systemically acts as an agonist on the naloxone-sensitive sigma receptor for attenuating the (−)-morphine-produced antinociception. The finding is consistent with the report by Chien and Pasternak (1994) *J. Pharmacol. Exp. Ther.* 271, 1583-1590, that systemic administration of sigma receptor agonist (+)-pentazocine (5 or 10 mg/kg) antagonizes (−)-morphine-produced analgesia. The attenuation of morphine analgesic effect can be reversed by sigma receptor antagonist haloperidol. (+)-Pentazocine given supraspinally but not spinally attenuates the antinociception produced by (−)-morphine given supraspinally. The anti-opioid effect by (+)-pentazocine is non-selective, which can attenuate the antinociceptive effect produced by δ- and κ-opioid agonists as well. Co-administration with sigma antagonist haloperidol potentiates (−)-morphine-produced analgesic effect indicating the anti-opioid sigma system is tonically active. Applicants also found in the present study the (+)-pentazocine given spinally did not affect the antinociception produced by (−)-morphine, which is in line with previous reports (Mei and Pasternak, 2002), and surprisingly reversed the attenuation of the (−)-morphine-produced antinociception induced by (+)-morphine. These observations demonstrate that it is sigma receptor agonist e.g. (+)-pentazocine and (+)-morphine elicit antianalgesic effect against (−)-morphine and other opioid agonists.

Surprisingly, (+)-pentazocine, a known selective sigma receptor agonist, also dose-dependently reversed (+)-morphine-induced antianalgesic effect co-administered spinally. Mei and Pasternak (2002) conclude that supraspinal site is the active site of (+)-pentazocine-induced anti-opioid effect based on the findings that (+)-pentazocine (13 μg) is without effect against morphine (700 ng) when both were given spinally in mice. When given systemically or supraspinally, (+)-pentazocine acts as a sigma receptor agonist to induce antianalgesic effect against opioid agonists such as (−)-morphine when given systemically or supraspinally. On the other hand, (+)-pentazocine acts as a sigma antagonist or partial agonist given spinally to antagonized (+)-morphine-induced antianalgesic effect against (−)-morphine given spinally. Why (+)-pentazocine has such dual effects? The discrepancies may be due to different route of drug administration (site dependent) and possible different receptor mechanism (effect dependent; naloxone-sensitive sigma receptor vs. sigma-1 receptor). The results disclosed herein with (+)-pentazocine provides additional evidence that (+)-morphine attenuates the (−)-morphine-produced antinociception via the naloxone-sensitive sigma-receptors in the mouse spinal cord.

The disclosure of every patent, patent application, and publication cited herein is hereby incorporated herein by reference in its entirety.

It is understood that certain adaptations of the invention described in this disclosure are a matter of routine optimization for those skilled in the art, and can be implemented without departing from the spirit of the invention, or the scope of the appended claims.

I claim:

1. A method of treating addiction in an individual comprising the step of administering to the addicted individual a therapeutically effective amount of pharmacologically active compound comprising dextro-morphine, which is capable of activating a sigma receptor, wherein the addiction is to an opioid.

2. The method in claim 1, wherein the opioid is an opiate.

3. The method of claim 1, wherein the opioid comprises a natural opiate, a semi-synthetic opiate, a fully synthetic opioid, an endogenous opioid peptide, or a combination thereof.

4. The method of claim 3, wherein the natural opiate is selected from a member of the group consisting of opium alkaloids, (−)-morphine, opium, and codeine.

5. The method of claim 3, wherein the semi-synthetic opiate is selected from a member of the group consisting of hydromorphone, hydrocodone, oxycodone, and heroin.

6. The method of claim 3, wherein the fully synthetic opiod is selected from a member of the group consisting of fentanyl, pethidine, methadone, and propoxyphene.

7. The method of claim 3, wherein the endogenous opioid peptide is selected from a member of the group consisting of endorphins, enkephalins, dynorphins, and endomorphins.

8. The method of claim 2, wherein the opiate is (−)-morphine.

9. The method of claim 1, wherein the individual is a mammal.

10. The method of claim 1, wherein the individual is a human.

11. The method of claim 1, wherein the route of administration is selected from the group consisting of oral, intraperitoneal, parenteral, intravenous, intrathecal, and transdermal.

12. The method of claim 1, wherein the dextro-morphine is administered to the individual prior to, simultaneously with or subsequent to taking the addictive opioid.

13. The method of claim 1, wherein the dextro-morphine is administered by pulse-dosing, wherein the pulse-dosing is repeated as needed in a human.

14. The method of claim 10, wherein the human is pretreated with an effective dose of dextro-morphine, wherein the pretreatment dosage ranges from about 1 μg/kg to about 5 μg/kg given subcutaneously.

15. The method of claim 10, wherein the human is pretreated with an effective dose of dextro-morphine, wherein the pretreatment dosage ranges from about 0.2 μg/kg to about 1 μg/kg given intraveneously.

16. The method of claim 10, wherein the human is pretreated with an effective dose of dextro-morphine, wherein the pretreatment dosage ranges from about 5 μg/kg to about 25 μg/kg given orally.

17. The method of claim 10, wherein the human is pretreated with an effective dose of dextro-morphine, wherein the pretreatment dosage ranges from about 1.0 μg/kg to about 5 μg/kg given intraperitoneally.

18. The method of claim 1, wherein the dextro-morphine is administered as a single or multiple dose daily of about 0.5 mg to about 5 mg in a human.

19. The method of claim 14, wherein the pretreatment dosage is implanted into the human.

20. The method of claim 15, wherein the pretreatment dosage is injected into the human.

21. The method of claim 16, wherein the pretreatment dosage is ingested by the human.

* * * * *